(12) United States Patent
Kibbe et al.

(10) Patent No.: US 9,707,281 B2
(45) Date of Patent: Jul. 18, 2017

(54) PHARMACEUTICAL COMPOSITIONS AND METHODS FOR DIGESTING ATHEROSCLEROTIC PLAQUES

(71) Applicant: Northwestern University, Evanston, IL (US)

(72) Inventors: Melina R. Kibbe, Chicago, IL (US); Guillermo A. Ameer, Chicago, IL (US); Vinit N. Varu, Chicago, IL (US)

(73) Assignee: Northwestern University, Evanston, IL (US)

( * ) Notice: Subject to any disclaimer, the term of this patent is extended or adjusted under 35 U.S.C. 154(b) by 0 days.

(21) Appl. No.: 14/326,904

(22) Filed: Jul. 9, 2014

(65) Prior Publication Data

US 2014/0322190 A1    Oct. 30, 2014

Related U.S. Application Data

(62) Division of application No. 13/641,375, filed as application No. PCT/US2011/032530 on Apr. 14, 2011, now abandoned.

(60) Provisional application No. 61/323,954, filed on Apr. 14, 2010.

(51) Int. Cl.

| | | |
|---|---|---|
| *A61K 38/48* | (2006.01) | |
| *A61K 38/49* | (2006.01) | |
| *A61K 38/54* | (2006.01) | |
| *A61M 37/00* | (2006.01) | |
| *A61B 17/22* | (2006.01) | |
| *A61K 31/724* | (2006.01) | |
| *A61K 45/06* | (2006.01) | |
| *A61M 25/10* | (2013.01) | |
| *A61K 9/00* | (2006.01) | |

(52) U.S. Cl.
CPC ...... *A61K 38/4886* (2013.01); *A61B 17/2202* (2013.01); *A61K 31/724* (2013.01); *A61K 38/49* (2013.01); *A61K 38/54* (2013.01); *A61K 45/06* (2013.01); *A61M 25/1011* (2013.01); *A61M 37/0092* (2013.01); *C12Y 304/21068* (2013.01); *C12Y 304/24003* (2013.01); *C12Y 304/24024* (2013.01); *C12Y 304/24035* (2013.01); *A61K 9/0019* (2013.01)

(58) Field of Classification Search
None
See application file for complete search history.

(56) References Cited

U.S. PATENT DOCUMENTS

| | | | |
|---|---|---|---|
| 6,099,730 | A | 8/2000 | Ameer et al. |
| 6,271,232 | B1 | 8/2001 | Campbell et al. |
| 6,699,470 | B1 | 3/2004 | Ameer et al. |
| 7,097,855 | B1 | 8/2006 | Ameer et al. |
| 7,141,045 | B2 | 11/2006 | Johansson et al. |
| 7,722,894 | B2 | 5/2010 | Wang et al. |
| 2003/0118692 | A1 | 6/2003 | Wang et al. |
| 2005/0053548 | A1 | 3/2005 | Strauss |
| 2005/0063939 | A1 | 3/2005 | Ameer et al. |
| 2006/0155178 | A1 | 7/2006 | Backman et al. |
| 2007/0071790 | A1 | 3/2007 | Ameer et al. |
| 2007/0208420 | A1 | 9/2007 | Ameer et al. |
| 2007/0224245 | A1 | 9/2007 | Ameer et al. |
| 2009/0035348 | A1 | 2/2009 | Zadini et al. |
| 2009/0148945 | A1 | 6/2009 | Ameer et al. |
| 2009/0208549 | A1 | 8/2009 | Berglund et al. |
| 2009/0325859 | A1 | 12/2009 | Ameer et al. |
| 2010/0034897 | A1 | 2/2010 | Ameer et al. |
| 2010/0036476 | A1 | 2/2010 | Ameer et al. |
| 2010/0076162 | A1 | 3/2010 | Ameer et al. |
| 2011/0071079 | A1 | 3/2011 | Ameer et al. |
| 2011/0082421 | A1 | 4/2011 | Ameer et al. |
| 2012/0225972 | A1 | 9/2012 | Ameer et al. |
| 2012/0237443 | A1 | 9/2012 | Ameer et al. |

OTHER PUBLICATIONS

Sigma-2, C0130 Collagenase Crude, Product Information, Sigma-Aldrich, St. Louis Missouri, available at www.sigmaaldrich.com/content/dam/sigma-aldrich/docs/Sigma/Product_Information_Sheet/c0130pis.pdf, web capture indicating publication in 2005 provided.*
Bond, "Purification and Separation of Individual Collagenases of Clostridium histolyticum Using Red Dye Ligand Chromatography", Biochemistry, 1984, 23:3077-3085.
Brinckerhoff et al., "Interstitial Collagenases as Markers of Tumor Progression", Clinical Cancer Research, 2000, 6:4823-4830.
Deguchi et al., "Matrix metalloproteinase-13/collagenase-3 deletion promotes collagen accumulation and organization in mouse atherosclerotic plaques", Circulation, 2005, 112:2708-2715.
Jong, "Role of ApoCs in Lipoprotein Metabolism", Arteriosclerosis, Thrombosis and Vascular Biology, 1999, 19:472-484.
Li et al., "Increased expression of 72-kd type IV collagenase(MMP-2) in human aortic atherosclerotic lesions", American Journal of Pathology, 1996, 148(1):121-128.
Shah et al., "Matrix Metalloproteinase Hypothesis of Plaque Rupture Players Keep Piling Up But Questions Remain", Circulation, 2001, 104:1878-1880.
Sigma, "Collagenase Guide" available at www.signmaaldrich.com/life-science/metabolomics/enzyme-explorer/learning-center/collagenase-guide.printerview.html, web capture from Dec. 26, 2008, courtesty of wayback machine provided.
Strauss et al., "Collagenase plaque digestion for facilitating guide wire crossing in chronic total occlusions", Circulation, 2003, 108:1259-1262.
International Search Report for PCT/US2011/032530 dated Dec. 29, 2011.
Written Opinion for PCT/US2011/032530 dated Dec. 29, 2011.
International Preliminary Report on Patentability for PCT/US2011/032530 dated Oct. 26, 2012.

* cited by examiner

*Primary Examiner* — Robert Yamasaki
*Assistant Examiner* — Charles Zoltan Constantine
(74) *Attorney, Agent, or Firm* — Andrus Intellectual Property Law, LLP

(57) ABSTRACT

Disclosed are pharmaceutical compositions and methods for digesting atherosclerotic plaques in a patient in need thereof. The compositions include and the methods utilize a mixture of collagenases for digesting plaques and optionally may include or utilize additional agents such as cyclodextrins, chelating agents, and tissue plasminogen activator.

11 Claims, 15 Drawing Sheets

PHARMACEUTICAL COMPOSITIONS AND METHODS FOR DIGESTING ATHEROSCLEROTIC PLAQUES

CROSS REFERENCE TO RELATED APPLICATIONS

The present application is a divisional of U.S. application Ser. No. 13/641,375, filed Dec. 4, 2012, which application was published on Aug. 1, 2013, as U.S. Publication No. 2013/0195828, and further which application is the U.S. national stage application of International Application PCT/US2011/032530, filed Apr. 14, 2011, which international application was published on Mar. 8, 2012, as International Publication WO2011/130537 in the English language. The International Application claims the benefit of priority to U.S. Provisional Application No. 61/323,954, filed Apr. 14, 2010, the contents of which are incorporated herein by reference in their entireties.

BACKGROUND

The field of the invention is related to cardiovascular disease including cardiovascular disease secondary to atherosclerosis and compositions and methods for treating or preventing cardiovascular disease secondary to atherosclerosis. The compositions and methods may be utilized for digesting atheroschlerotic plaques.

Cardiovascular disease secondary to atherosclerosis is the leading cause of death in the United States, accounting for 60% of total mortality in 2002. (See Rosamond W, et al. Circulation 2007; 115(5):E69-E171.) Approximately 16 million people in the United States have clinically manifested coronary heart disease, approximately 8 million have peripheral arterial disease, and over 5 million are stroke survivors. (See id.)

Atherosclerotic plaques evolve through a continuum of histological changes. Inflammation starts when endothelial cells become, activated and secrete adhesion molecules, and the vascular smooth muscle cells (VSMC) secrete chemokines and chemoattractants. Together, these agents attract monocytes, lymphocytes, mast cells, and neutrophils into the arterial wall. (See Katsuda S. et al. Arteriosclerosis and Thrombosis 1992; 12(4):494-502). VSMC also secrete into the extracellular matrix proteoglycans, collagen, and elastic fibers. Upon entry, monocytes transform into macrophages, take up lipids as multiple small inclusions, and become foam cells. Extracellular proteoglycans bind lipids and progressively increase their lipid-binding capacity by extension of their disaccharide arms. Some factors promote the death of macrophages and VSMC. The necrotic debris provokes further inflammation. Increasing accumulation of extracellular lipids coalesces into pools and causes cell necrosis. Fibrotic tissue forms a fibrous cap over the lipid-rich necrotic core. (See id.). New vaso vasorum with thin walls invade the diseased intima from the media. These fragile vessels of endothelium, lacking pericytes for support, may leak, producing hemorrhage within the arterial wall. These intramural hemorrhages provoke increased fibrous tissue deposition. Calcium deposits in the wall occur throughout all these steps, initially as small aggregates, and later as large nodules. (See Insull W. American Journal of Medicine 2009; 122(1):S3-S14). It is also known that type I, III, IV, V, and VI collagen are the main collagens within atherosclerotic plaques but the distribution varies by stage and progression of the lesion. (See Katsuda S. et al. Arteriosclerosis and Thrombosis 1992; 12(4):494-502). Thus, it is apparent that formation of atherosclerotic plaques follows a complex continuum of events.

Percutaneous vascular interventions and plaque debulking technology to treat the manifestations of cardiovascular disease secondary to atherosclerosis do exist. Currently available percutaneous therapies for severe atherosclerosis include angioplasty with or without stenting, cryoplasty, laser atherectomy, or remote atherectomy. The later category includes the use of the Silverhawk™ or Rockhawk Atherectomy™ devices, the Rotablator™, the Pathway Jetstream™, and the Diamondback Orbital Atherectomy™ system. Each of these therapies enlarges the lumen of the artery, thereby treating the underlying stenotic lesion. However, each of these therapies induces some form of trauma to the vascular wall. Angioplasty and stenting restores lumen patency by forcing the plaque against the wall of the artery under high pressure balloon inflations, thereby inducing significant trauma to the vascular wall Cryoplasty reduces plaque burden by initiating apoptosis of the cells in the atherosclerotic plaque by freezing these cells to a temperature of $-10°$ C. Laser atherectomy and mechanical remote atherectomy devices debulk the plaque but do so in association with high thermal temperatures. In fact, the Rotablator rotational atherectomy device was found to result in temperature increases of 2-4° C. with minimal decelerations, but increases of 11-14° C. with continuous ablation or rapid decelerations. Therefore, each of the current FDA approved therapies induces some form of mechanical injury to the vessel wall, which ultimately stimulates the development of neointimal hyperplasia and results in significant arterial restenosis. Furthermore, these therapies are costly, and require considerable time to debulk long segments of plaque. Therefore, new methodologies to reduce atherosclerotic plaques without inducing mechanical trauma to the arterial wall are desirable.

Here a new methodology for treating atherosclerotic lesions is proposed and developed through the optimization of a "digestion" solution that will result in non-traumatic in vivo digestion of atherosclerotic plaques. Given the fact that most atherosclerotic plaques are composed of lipids, proteoglycans, collagens, and calcium deposits, it is hypothesized that a "digestion" solution containing agents that specifically target these plaque components will dissolve and digest the plaque in vivo within a clinically relevant time frame, thereby allowing its use alone or in combination with other therapeutic interventions. Ultimately, the optimized digestion solution may be administered via a double balloon occlusion catheter to an isolated segment in the vasculature percutaneously.

This proposed approach to treating severe atherosclerosis percutaneously is innovative, as no therapy exists on the market that is even remotely similar. Devices exist that debulk atherosclerotic plaques, as described above. However, each of these devices induces some form of thermal or mechanical trauma to the arterial wall. The presently disclosed plaque digestion therapy is unique in that it will result in plaque debulking without inducing any trauma to the vascular wall. Thus, this therapy, when successfully developed, has great potential to have a large impact in the clinical arena, given the prevalence of interventions for atherosclerosis.

SUMMARY

Disclosed are compositions and methods for treating a patient having or at risk for developing cardiovascular disease, including cardiovascular disease secondary to atheroschlerosis. The disclosed compositions and methods may include pharmaceutical compositions and therapeutic methods for treating atheroschlerotic plaques.

The disclosed compositions may include pharmaceutical compositions comprising: (a) a mixture of collagenases comprising one, two, three, four, or more collagenases (e.g., collagenase type I, collagenase type III, collagenase type IV, and collagenase type V); and (b) a carrier. Preferably, the collagenases are present in the composition at concentrations that are sufficient for digesting a human arterial plaque and reducing mass of the human arterial plaque by at least 30% (preferably at least 40%, 50%, 60%, 70%, 80%, or 90%) after the sample is contacted with the composition for no more than about 2 hours (preferably for no more than about 1 hour, or more preferably for no more than 30, 20, 10, or 5 minutes). For example, preferably the collagenases are present in the composition at concentrations that are sufficient for digesting a human arterial plaque and reducing mass of the human arterial plaque by at least 30% after the sample is contacted with the composition for no more than 10 minutes.

The disclosed compositions may include a mixture of collagenases comprising one, two, three, four, or more collagenases. In some embodiments, the compositions may comprise each of collagenase type I, collagenase type III, collagenase type IV, and collagenase type V at a suitable concentration (e.g., each at a concentration of at least about 0.1 mg/ml (preferably at a concentration of at least about 0.2 0.3, 0.4, 0.5, 0.6, 0.7, 0.8, 0.9, 1, 2, 4, 6, 8, 10, 20, 30, 40, or 50 mg/ml)). Suitable concentrations ranges may concentrations ranges within about 0.1-50 mg/ml (e.g., 0.2-0.8 mg/ml). In some embodiments, the pharmaceutical composition may comprise additional collagenases. In other embodiments, the pharmaceutical composition may comprise a collagenase mixture consisting of one or more of the following collagenases: collagenase type I, collagenase type III, collagenase type IV, and collagenase type V, and the composition includes no other collagenase.

The pharmaceutical compositions disclosed herein may include additional ingredients for digesting or dissolving atheroschlerotic plaques. In some embodiments, the pharmaceutical compositions further comprise, a cyclodextrin (e.g., alpha-, beta-, or gamma-cyclodextrin and preferably beta-cyclodextrin). The pharmaceutical composition may comprise the cyclodextrin at a suitable concentration. Suitable concentration ranges may include, but are not limited to, a range of about 1-100 mM, and preferably a range of about 5-25 mM.

The pharmaceutical compositions disclosed herein may comprise a chelating agent for a divalent cation (e.g., EDTA). The pharmaceutical composition may comprise the chelating agent at a suitable concentration. Suitable concentration ranges may include, but are not limited to, a range of about 0.5 mg/ml-2 mg/ml, and preferably a range of about 0.75-1.25 mg/ml.

The pharmaceutical compositions disclosed herein may comprise a divalent cation (e.g., $Ca^{2+}$). The divalent cation may be added to the composition as a salt. In some embodiments, the compositions comprise $Ca^{2+}$ at a concentration of about 1-25 mM.

The pharmaceutical compositions disclosed herein may comprise cholesterol esterase at a suitable concentration for hydrolyzing cholesterol esters, triacylglycerols, phospholipids, ceramides, lysophospholipids, or a mixture thereof in a human arterial plaque. Suitable concentration ranges may include, but are not limited to, a range of about 0.1-10 Units/ml.

The pharmaceutical compositions disclosed herein may comprise lipoprotein lipase at a suitable concentration for hydrolyzing lipids into free fatty acids and monoacylglycerol in a human arterial plaque. Suitable concentration ranges may include, but are not limited to, a range of about 30-10,000 units/ml.

The pharmaceutical compositions disclosed herein further may comprise apolipoprotein CII at a suitable concentration for functioning as a co-factor for lipoprotein lipase. Suitable concentration ranges may include, but are not limited to, a range of about 1-20 units/ml.

The pharmaceutical compositions disclosed herein may comprise pepsin at a suitable concentration for digesting carbon bonds in proteins by cleaving preferentially after the N-terminal of aromatic amino acids such as phenylalanine, tryptophan, and tyrosine. Suitable concentration ranges may include, but are not limited to, a range of about 1-50 mg/ml.

The pharmaceutical compositions disclosed herein may comprise phospholipase A2 at a suitable concentration, for hydrolyzing glycerol in human arterial plaque by releasing fatty acids from the second carbon group of glycerol.

The pharmaceutical compositions disclosed herein may comprise tissue plasminogen activator (tPA) at a suitable concentration for converting plasminogen to plasmin. Suitable concentration ranges may include, but are not limited to, a range of about 0.5-20 mg/ml (preferably a range of about 0.5-2 mg/ml, and more preferably a range of about 0.75-1.25 mg/ml).

The pharmaceutical compositions disclosed herein preferably have a suitable pH for physiological conditions. For example, the pharmaceutical composition may have a pH within a range of about 7-8 (and preferably within a range of about 7.2-7.6).

The disclosed compositions may be utilized in methods for treating a patient having or at risk for developing cardiovascular disease. The disclosed compositions may be utilized in methods for treating a patient having or at risk for developing atherosclerosis or atherosclerotic plaques. In some embodiments, the disclosed methods include methods for digesting a human arterial plaque in a patient, the methods comprising contacting the plaque with a pharmaceutical composition as contemplated herein (e.g., a pharmaceutical composition comprising (a) a mixture of collagenases comprising one, two, three, four or more collagenases (e.g., collagenase type I, collagenase type III, collagenase type IV, and collagenase type V); and (b) a carrier). Preferably, the collagenases are present in the composition at concentrations that are sufficient for digesting a human arterial plaque and reducing mass of the human arterial plaque by at least about 30% (preferably at least 40%, 50%, 60%, 70%, 80%, or 90%) after the sample is contacted with the composition for no more than about 2 hours, 1 hour, 50 minutes, 40 minutes, 30 minutes, 20 minutes, 10 minutes, or preferably 5 minutes. In some embodiments of the methods, the pharmaceutical composition is administered to the patient via a double-balloon occlusion catheter whereby the composition contact an atherosclerotic plaque in the patient and dissolves or digests at least a portion of the plaque. The composition then is aspirated from the site of the plaque together with any dissolved, digested, or dislodged plaque material. Optionally, the site subsequently may be washed with a saline solution and further aspirated to remove any additional dissolved, digested, or dislodged plaque material.

In some embodiments of the disclosed methods, the methods include administering a first solution to a patient and then subsequently administering a second solution to the patient, before, concurrently with, or subsequently to administering the first solution. The first solution and the second solution may be the same or different. For example, the first solution may be a dissolution solution and the second solution may be a digestion solution, where the dissolution solution may comprise one or more of the following agents, a cyclodextrin, a chelating agent, calcium, and tPA, cholesterol esterase, lipoprotein lipase, apolioprotein CII, pepsin, phospholipase A2, or mixtures thereof, and the digestion solution comprises one or more of the following collagenases: collagenase type I, collagenase type III, collagenase type IV, and collagenase type V. The first solution and the second solution typically are administered via a double balloon occlusion catheter whereby the first solution and the second solution contact an atheroschlerotic plaque in the patient. The first solution and the second solution then are aspirated from the site of the plaque together with any dissolved, digested, or dislodged plaque material. Optionally, the site subsequently may be washed with a saline solution and further aspirated to remove any additional dissolved, digested, or dislodged plaque material.

In some embodiments of the disclosed methods, the methods include administering ultrasonic energy to a patient, e.g., at the site of an arterial plaque. Ultrasonic energy may be administered at the site of the arterial plaque before, during, or after contacting the arterial plaque with the pharmaceutical compositions disclosed herein. Preferably, the ultrasonic energy facilitates dissolution of the arterial plaque. The ultrasonic energy may have a suitable frequency and may be administered for a suitable period of time to facilitate dissolution of the plaque.

DETAILED DESCRIPTION

Figure 1:
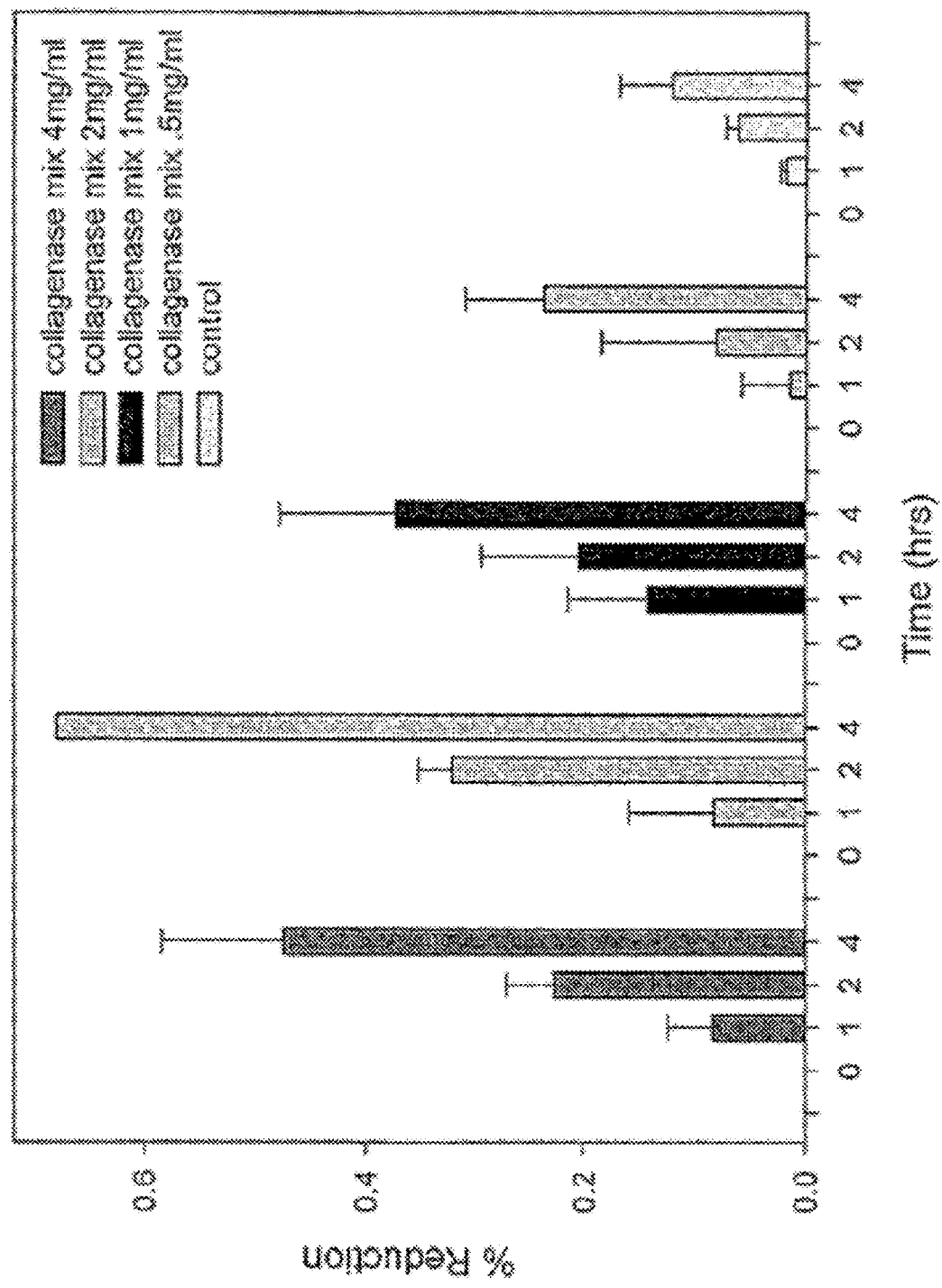
FIG. 1. illustrates digestion of atherosclerotic plaques after exposure to different concentrations of a mixture of type I, III, IV, and V collagenases at 37 degrees Celsius and pH 7.4. The optimal concentration for digestion at 2- and 4-hour time points is 2 mg/ml, but all concentrations were able to fully digest the plaques by 24 hours.

The subject matter disclosed herein is described using several definitions, as set forth below and throughout the application.

Unless otherwise noted, the terms used herein are to be understood according to conventional usage by those of ordinary skill in the relevant art. In addition to the definitions of terms provided below, it is to be understood that as used in the specification, embodiments, and in the claims, "a", "an", and "the" can mean one or more, depending upon the context in which it is used.

As used herein, "about," "approximately," "substantially," and "significantly" will be understood by persons of ordinary skill in the art and will vary to some extent on the context in which they are used. If there are uses of the term which are not clear to persons of ordinary skill in the art given the context in which it is used, "about" or "approximately" will mean up to plus or minus 10% of the particular term and "substantially" and "significantly" will mean more than plus or minus 10% of the particular term.

As used herein, the terms "include" and "including" have the same meaning as the terms "comprise" and "comprising."

As used herein, the term "patient" may be used interchangeable with the term "subject" and means an animal, which may be a human or non-human animal, in need of treatment. Non-human animals may include dogs, cats, horses, cows, pigs, sheep, and the like.

A "patient in need thereof" may include a patient having or at risk for developing cardiovascular disease (e.g., cardiovascular disease secondary to atheroschlerosis). A patient in need thereof may refer to a patient having or at risk for acquiring an arterial disease or disorder such as atherosclerosis or atherosclerotic plaques. A patient in need thereof may refer to a patient having or at risk for acquiring neointimal hyperplasia or acute arterial thrombosis. A patient in need thereof may refer to a patient having recently undergone an angioplasty procedure.

As used herein, the phrase "therapeutically effective amount" shall mean that dosage of an active agent that provides the specific pharmacological response for which the active agent is administered in a significant number of subjects in need of such treatment. A therapeutically effective amount of an active agent that is administered to a particular subject in a particular instance will not always be effective in all instances for treating the conditions/diseases described herein, even though such dosage is deemed to be a therapeutically effective amount in particular instances by those of skill in the art.

The compositions disclosed herein may be formulated as pharmaceutical compositions. For example, pharmaceutical compositions disclosed herein may include a carrier, excipient, or diluent (i.e., agents), which are nontoxic to the cell or mammal being exposed thereto at the dosages and concentrations employed. Often a physiologically acceptable agent is an aqueous pH buffered solution. Examples of physiologically acceptable carriers include buffers such as phosphate, citrate, and other organic acids; antioxidants including ascorbic acid; low molecular weight (less than about 10 residues) polypeptide; proteins, such as serum albumin, gelatin, or immunoglobulins; hydrophilic polymers such as polyvinylpyrrolidone; amino acids such as glycine, glutamine, asparagine, arginine or lysine; monosaccharides, disaccharides, and other carbohydrates including glucose, mannose, or dextrins; chelating agents such as EDTA; sugar alcohols such as mannitol or sorbitol; salt-forming counterions such as sodium; and/or nonionic surfactants such as TWEEN™, polyethylene glycol (PEG), and PLURONICS™.

The disclosed compositions may be administered to a patient via the use of a multiple balloon catheter as known in the art. For example, multiple balloon catheters are disclosed in U.S. Pat. No. 5,514,092, the content of which is incorporated herein by reference in its entirety.

In some embodiments of the methods disclosed herein, the methods include administering ultrasonic energy to a patient, e.g., administering ultrasonic energy at the site of an arterial plaque in the patient. Ultrasonic energy may be administered at the site of the arterial plaque before, during, or after contacting the arterial plaque with the pharmaceutical compositions disclosed herein. Preferably, the ultrasonic energy has a suitable frequency (e.g., 1-1000 kHz, more preferably 5-500 kHz, even more preferably 10-100 kHz) and may be administered for a suitable period of time to facilitate dissolution of the plaque (e.g., for 0-60, 0-50, 0-40, 0-30, 0-20, 0-10, or 0-5 minutes.).

Ultrasonic energy may be administered to the arterial plaque using methods known in the art. The use of ultrasound has also been demonstrated to reduce atherosclerotic burden. Goyen et al. reported the use of an intra-arterial ultrasound catheter to debulk atherosclerotic chronic total occlusions ("Intravascular ultrasound angioplasty in peripheral arterial occlusion. Preliminary experience." Acta Radiol. 2000; 41(2)122-124, the content of which is incorporated herein by reference in its entirety.) Using fluoroscopic guidance, an over-the-wire catheter containing piezoelectric elements at its tip that convert electrical energy into ultrasound energy was slowly advanced through chronic total occlusion. The transmitter emitted continuous ultrasound frequency of 42 kHz. During activation of the device, the catheter tip was irrigated continuously with saline (8 ml/min) to remove debris. The authors reported 100% technical success in all 9 patients. The ultrasound catheter created a channel through the atherosclerotic plaque that was twice the diameter of the transmitter. The remaining plaque was treated with aspiration thrombectomy or balloon angioplasty.

ILLUSTRATIVE EMBODIMENTS

The following embodiments are illustrative and are not intended to limit the scope of the claimed subject matter.

Embodiment 1

A pharmaceutical composition comprising: (a) a mixture of two, three, four or more collagenases (e.g., collagenase type I, collagenase type III, collagenase type IV, and collagenase type V); and (b) a carrier.

Embodiment 2

The pharmaceutical composition of embodiment 1, wherein the collagenases are present in the composition at concentrations that are sufficient for digesting a human arterial plaque and reducing mass of the human arterial plaque by at least 30% (preferably at least 40%, 50%, 60%, 70%, 80%, or 90%) after the sample is contacted with the composition for no more than about 2 hours, 1 hour, 30, 20, 10, or 5 minutes.

Embodiment 3

The pharmaceutical composition of embodiment 1 or 2, comprising each of collagenase type I, collagenase type III, collagenase type IV, and collagenase type V at a concentration of at least about 0.1 mg/ml (preferably at a concentration of at least about 0.2, 0.3, 0.4, 0.5, 0.6, 0.7, 0.8, 0.9, 1, 2, 4, 6, 8, 10, 20, 30, 40, or 50 mg/ml).

Embodiment 4

The pharmaceutical composition of any of embodiments wherein the mixture of collagenases consists of collagenase type I, collagenase type collagenase type IV, and collagenase type V.

Embodiment 5

The pharmaceutical composition of any of embodiments 1-4, further comprising a cyclodextrin (e.g., alpha-, beta-, or gamma-cyclodextrin and preferably beta-cyclodextrin).

Embodiment 6

The pharmaceutical composition of embodiment 5, wherein the cyclodextrin is present at a concentration of 1-100 mM (preferably 5-25 mM).

Embodiment 7

The pharmaceutical composition of any of embodiments 1-6, further comprising a chelating agent (e.g., EDTA).

Embodiment 8

The pharmaceutical composition of embodiment 7, wherein the cheating agent is present at a concentration of 0.5 mg/ml-2 mg/ml (preferably 0.75-1.25 mg/ml).

Embodiment 9

The pharmaceutical composition of any of embodiments 1-8, further comprising tissue plasminogen activator.

Embodiment 10

The pharmaceutical composition of embodiment 9, wherein the tissue plasminogen activator is present at a concentration of 0.5-20 mg/ml (preferably 0.75-1.25 mg/ml).

Embodiment 11

The pharmaceutical composition of any of embodiments 1-10, further comprising cholesterol esterase (preferably at a concentration of 0.1-10 units/ml).

Embodiment 12

The pharmaceutical composition of any of embodiments 1-11, further comprising lipoprotein lipase (preferably at a concentration of 30-10,000 units/ml).

Embodiment 13

The pharmaceutical composition of any of embodiments 1-12, further comprising apolipoprotein CII (preferably at a concentration of 1-20 units/ml).

Embodiment 14

The pharmaceutical composition of any of embodiments 1-13, further comprising phospholipase A2.

Embodiment 15

The pharmaceutical composition of any of embodiments 1-14, further comprising pepsin (preferably at a concentration of 1-50 mg/ml).

Embodiment 16

The pharmaceutical composition of any of embodiments 1-15, wherein the composition has a pH of about 7-8 (preferably about 7.2-7.6).

Embodiment 17

A method for digesting a human arterial plaque in a patient, the method comprising contacting the plaque with a pharmaceutical composition comprising: (a) a mixture of collagenases comprising two, three, four or more collagenases (e.g., collagenase type I, collagenase type III, collagenase type IV, and collagenase type V); and (b) a carrier.

Embodiment 18

The method of embodiment 17, wherein the collagenases are present in the composition at concentrations that are sufficient for digesting a human arterial plaque and reducing weight of a sample of the human arterial plaque by at least 30% (preferably at least 40%, 50%, 60%, 70%, 80%, or 90%) after the sample is contacted with the composition for no more than about 2 hours, 1 hour, 30, 20, 10, or 5 minutes.

Embodiment 19

The method of embodiment 17 or 18, comprising each of collagenase type I, collagenase type III, collagenase type IV, and collagenase type V at a concentration of at least about 0.1 mg/ml (preferably at a concentration of at least about 0.2, 0.3, 0.4, 0.5, 0.6, 0.7, 0.8, 0.9, 1, 2, 4, 6, 8, 10, 20, 30, 40, or 50 mg/ml).

Embodiment 20

The method of any of embodiments 17-19, wherein the mixture of collagenases consists of collagenase type I, collagenase type III, collagenase type IV, and collagenase type V.

Embodiment 21

The method of any of embodiments 17-20, further comprising a (e.g., alpha-, beta-, or gamma-cyclodextrin and preferably beta-cyclodextrin).

Embodiment 22

The method of embodiment 21, wherein the cyclodextrin is present at a concentration of 1-100 mM (preferably 5-25 mM).

Embodiment 23

The method of any of embodiments 17-22, further comprising a chelating agent EDTA).

Embodiment 24

The method of embodiment 23, wherein the chelating agent is present at a concentration of 0.5 mg/ml-2 mg/ml (preferably 0.75-1.25 mg/ml).

Embodiment 25

The method of any of embodiments 17-24, further comprising tissue plasminogen activator.

Embodiment 26

The method of embodiment 25, wherein the tissue plasminogen activator is present at a concentration of 0.5-20 mg/ml (preferably 0.75-1.25 mg/ml).

Embodiment 27

The method of any of embodiments 17-26, further comprising cholesterol esterase (preferably at a concentration of 0.1-10 units/ml).

Embodiment 28

The method of any of embodiments 17-27, further comprising lipoprotein lipase (preferably at a concentration of 30-10,000 units/ml).

Embodiment 29

The method of any of embodiments 17-28, further comprising apolipoprotein CII (preferably at a concentration of 1-20 units/ml).

Embodiment 30

The method of any of embodiments 17-29, further comprising phospholipase A2.

Embodiment 31

The method of any of embodiments 17-30, further comprising pepsin (preferably at a concentration of 1-50 mg/ml).

Embodiment 32

The method of any of embodiments 17-31, wherein the composition has a pH of about 7-8 (preferably about 7.2-7.6).

Embodiment 33

The method of any of embodiments 17-32, wherein the composition is administered to the patient via a double-balloon catheter.

Embodiment 34

The method of any of embodiments 17-33, wherein the composition is contacted with the human arterial plaque for at least 1 hour (or at least 2 hours or 4 hours).

Embodiment 35

The method of any of embodiments 17-34, further comprising applying ultrasonic energy to the plaque.

Embodiment 36

A method of treating an atherosclerotic plaque in a patient, the method comprising administering a collagenase composition comprising two, three, four or more collagenases to the patient at the site of the atherosclerotic plaque via a double balloon occlusion catheter.

Embodiment 37

The method of embodiment 36, wherein the collagenase composition comprises a combination of collagenase types I, III, IV, and V.

Embodiment 38

The method of embodiment 36, wherein the collagenase composition comprises 0.5-50 mg/ml of each of collagenase types I, III, IV, and V.

Embodiment 39

The method of embodiment 36, wherein the collagenase composition comprises 1.0-10 mg/ml of each of collagenase types I, III, IV, and V.

Embodiment 40

The method of any of embodiments claim 36-39, further comprising administering a composition comprising tissue plasminogen activator (tPa), before, during, or after administering the collagenase composition.

Embodiment 41

The method of any of embodiments 36-40, further comprising administering a composition comprising a cyclodextrin, before, during, or after administering the collagenase composition.

Embodiment 42

The method of embodiment 41, wherein the cyclodextrin is beta-cyclodextrin.

Embodiment 43

The method of any of embodiments 36-42, further comprising administering a composition comprising a chelator, before, during, or after administering the collagenase composition.

Embodiment 44

The method of any of embodiments 36-43, further comprising administering a composition comprising tissue plasminogen activator (tPa), before, during, or after administering the collagenase composition.

Embodiment 45

The method of any of embodiments 36-44, further comprising administering a composition comprising cholesterol esterase, before, during, or after administering the collagenase composition.

Embodiment 46

The method of any of embodiments 36-45, further comprising administering a composition comprising lipoprotein lipase, before, during, or after administering the collagenase composition.

Embodiment 47

The method of any of embodiments 36-46, further comprising administering a composition comprising apolipoprotein CII, before, during, or after administering the collagenase composition.

Embodiment 48

The method of any of embodiments 36-47, further comprising administering a composition comprising phospholipase A2, before, during, or after administering the collagenase composition.

Embodiment 49

The method of any of embodiments 36-48, further comprising administering a composition comprising, comprising pepsin, before, during, or after administering the collagenase composition.

Embodiment 50

The method of any of embodiments 36-49, further comprising applying ultrasonic energy to the plaque.

EXAMPLES

The following examples are illustrative and are not intended to limit the scope of the disclosed and claimed subject matter.

Example 1—Digestion and Dissolution Solutions for Arterial Plaques

Background.

The present disclosure outlines a new and unique method of removing atherosclerotic plaque from arteries. Cardiovascular disease, predominately secondary to atherosclerosis, is the leading cause of death in the United States, accounting for 60% of total mortality in 2002. Percutaneous vascular procedures that treat severe atherosclerosis often utilize balloon angioplasty, which is the expansion of a balloon inside the narrowed artery to increase the lumenal area followed by deployment of a rigid or non-compliant metal stent to prevent the elastic recoil that occurs following balloon angioplasty. While this technique is commonplace, it fails to remove or reduce the atherosclerotic plaque burden. The remaining plaque burden, along with the stimulation of the arterial injury response by balloon angioplasty, result in significant restenosis rates, requiring further interventions or surgery, or myocardial infarction, limb loss, or death. While drug-eluting stents have demonstrated a significant reduction in restenosis rates, its safety has come under question due to increased rates of late stent thrombosis. Here, new methods for treating atherosclerosis are proposed via optimizing in vivo "digestion" of atherosclerotic plaques, thereby removing atherosclerotic plaque burden. It is hypothesized that by removing the plaque burden, and by avoiding the use of balloon angioplasty and its associated activation of the arterial injury cascade, restenosis rates following this approach will be dramatically decreased compared to all current interventions aimed to treat severe atherosclerosis.

Atherosclerotic plaques form over the course of several decades through a process of cholesterol deposition, inflammatory responses, lipid accumulation, and extracellular matrix production. In the center of the atherosclerotic lesions, foam cells and extracellular lipids form a core region, which is surrounded by a fibrous cap of smooth muscle cells and a collagen rich matrix. The devastating consequences of atherosclerosis occur when the fibrous cap ruptures, exposing the thrombogenic core to the blood, initiating coagulation with subsequent thrombosis of the vessel. Studies have revealed that plaques are not uniform when examined between patients. Stary et al. have classified plaques based on their different characteristics: (I) Lipid-laden macrophages present as only isolated groups; (II) Lipid-laden macrophages stratified as adjacent layers; (III) Macrophages, extracellular accumulation of lipids; (IV) Lipid core without fibrous tissue or fissure formation; (V) Smooth muscle cells, extracellular matrix (collagen, glycoproteins, proteoglycans); (Va) Fibrous tissue, lipids; (Vb) Prominent calcific component; (Vc) Prominent fibrous component; and (VI) Hemorrhage, fissure, (see Stary H C, et al., Circulation 1995; 92(5): 1355-1374.

Using collagen type-specific antibodies, it is also known that type I, III, IV, V, and VI are the main collagens within atherosclerotic plaques, with the amount of distribution varying on the stage and progression of the lesion. Here, new methods for treating atherosclerotic lesions are proposed through optimization of a "digestion" solution that would promote in vivo digestion of atherosclerotic plaques. Given the fact that most rigid plaques are consistently composed of lipids, proteoglycans, collagens, and calcium deposits, it is hypothesized that a "digestion solution" containing agents that specifically target plaque components will be able to dissolve and digest the plaque in viva in an accelerated amount of time. Furthermore, since the intimal layer of the arterial wall is separated from the medial layer by the internal elastic lamina, avoidance of the use of elastases will limit the plaque digestion to just the intimal layer, thereby preserving the medial layer of the arterial wall and safely limiting the reaction in vivo.

Currently, the mainstay of therapy for severe atherosclerosis consists of percutaneous balloon angioplasty with or without stenting, surgical bypass grafting, or surgical endarterectomy, the later of which removes the plaque burden surgically. The number of procedures performed annually for percutaneous approaches for the treatment of severe atherosclerosis greatly out number that of open surgery. In the current era of endovascular options, many different percutaneous approaches exist. However, balloon angioplasty with or without stenting remains the most common approach utilized. This approach is plagued by the fact that the atherosclerotic plaque is not removed, but mechanically compressed against the arterial wall. The high inflation pressures required to accomplish this in turn stimulates the arterial injury response in the vascular wall, which results in the development of neointimal hyperplasia that ultimately re-occludes the vessel. Thus, this procedure which aims to increase lumen area actually results in its own failure. For a long time, researchers have been trying to develop methods to debulk atherosclerotic plaques. Many different devices have been introduced into the market. Today, only a few debulking devices exist that are FDA approved. These include the Rotoblader™, the Silverhawk™, the Rockhawk™, the Diamondback™, and the Jetstream™ device. Each of these devices mechanically removes or debulks the plaque either through the use of an oscillating blade that pulverizes the plaque or the use of a blade that shaves the plaque. Each of these devices has drawbacks that limits it use, and none have proven to be superior to conventional balloon angioplasty and stenting in large, prospective, randomized clinical trials.

The presently proposed methods aim to remove the plaque burden with minimal trauma to the arterial wall and minimal risk to the patient. The present inventors are unaware of these proposed methods ever having been performed in patients. The proposed methods do not require the use of balloons or mechanical blades for contacting the plaque, thus avoiding the potential risk of inducing arterial injury and at the same time providing a safe approach. All particulate matter will be aspirated, thereby avoiding embolization of atherosclerotic plaque, a problem that all of the above-mentioned atherectomy devices face. Thus, when our approach is utilized, we expect superior outcomes that are associated with significantly reduce failure rates compared to currently available modalities, thereby diminishing the need for reintervention, improving patient outcomes, and reducing overall health care costs.

Materials, Methods, and Results.

Atherosclerotic plaques from surgical endarterectomies were obtained from various anatomic sites. All experiments were performed by cutting a given plaque into equal parts by weight then exposing them to various agents alone and in combination to determine the most optimal digestion solution. The optimal concentration and conditions for plaque dissolution and digestion were determined for ethylenediaminetetraacetic acid (EDTA), β-cyclodextrin, tPA, collagenase type I, III, IV, and V. Weights of each specimen were obtained prior to exposure of each solution and at different time points to determine percent of digested versus undigested plaque. Additional variables that were assessed and optimized include: 1) different combinations of EDTA, β-cyclodextrin, and the collagenases, 2) temperature, 3) pH, and 4) agitation.

Initially, a digestion solution comprising type I, III, IV, and V collagenase at a concentration of 2 mg/ml was determined to be optimal (68% reduction, $p<0.05$) (FIG. 1). Next, different parameters of the "digestion solution" were tested to determine if the efficiency of plaque digestion could be improved. Optimal conditions for the digestion solution were found to be a temperature of 37 degree Celsius (51% reduction, $p<0.05$), pH 7.4 (47% reduction, $p<0.05$), and agitation (61% reduction, $p<0.05$). Using these standardized conditions for digestion, plaque-to-plaque variability was assessed with no significant difference in amount of digestion between different plaque specimens.

Figure 2:
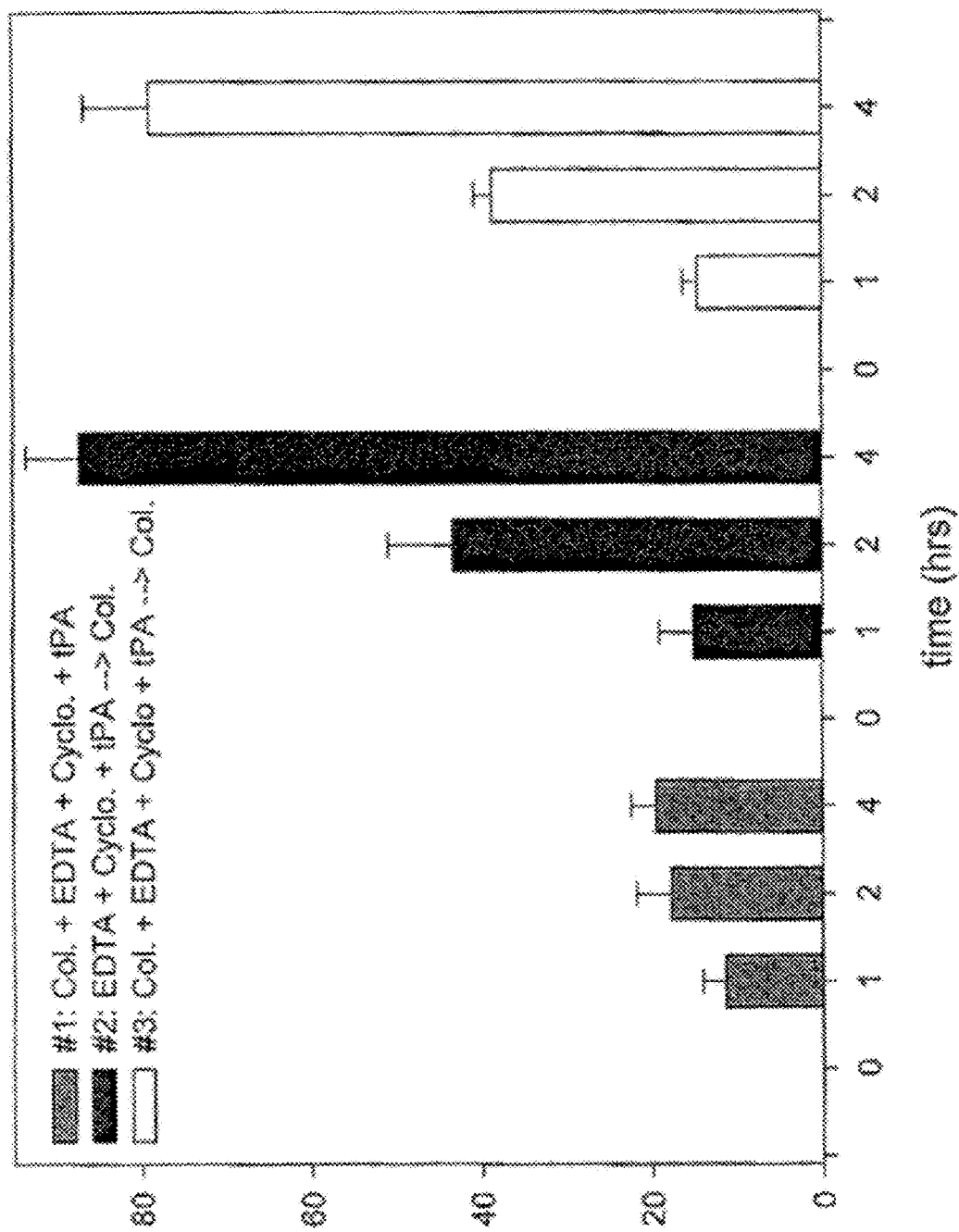
FIG. 2. illustrates digestion of atherosclerotic plaques after exposure to different combinations of EDTA (1 mg/ml). (β-cyclodextrin (Cyclo, 10 mMol), tPA (1 mg/ml) and Collagenase mixture type I, III, IV, V (Col, 2 mg/ml) at 37 degrees Celsius, 225 rpm agitation, and ph 7.4. The first combination (#1) consisted of all four reagents together at once. The second combination (#2) consisted of EDTA, {β-cyclodextrin, and tPA together, with removal of this solution at 1 hour, and then addition of the collagenase mixture. The third combination (#3) consisted of all four agents together at once, followed by removal of the solution at 1 hour, and then addition of the collagenase mixture. The most effective combination was #2 at 4 hours, though #3 was effective as well.

Next, agents that reacted with different components of the plaque were tested to further optimize digestion. The effect of localized chelation of calcium from the plaque was evaluated with exposure to EDTA. The effect of localized solubilization of extracellular lipid from the plaque was evaluated with exposure to β-cyclodextrin. And lastly, proteoglycans were dissolved by tissue plasminogen activator (tPA). Neither EDTA (0.5 mg/ml-2 mg/ml), β-cyclodextrin (1~100 mMol), or tPA (0.5-2 mg/ml) alone caused significant reduction in plaque weight (15%, 2%, 20%, respectively, p<0.05). But when combined with collagenase in different combination schemes at optimal standardized conditions, the percent digestion of plaque samples were improved (87% reduction at 4 hrs, p<0.05) (FIG. 2).

Ideally, the dissolution and digestion solutions and methods of administration will be further improved to reduce the time for digestion in vivo. However, the concept of using a dissolution and digestion solution to degrade an atherosclerotic plaque in vivo is sound and effective. It is expected that the presently disclosed solution will be used to treat patients with severe atherosclerosis percutaneously via delivery through the use of a double balloon occlusion catheter. The solution will be delivered after balloon occlusion is achieved. The space between the balloons will be irrigated with normal saline, the digestion solution will be injected for a predetermined period of time, the digestion solution along with plaque debris will be aspirated, and flow will be restored. The methods will reduce the atherosclerotic plaque burden with no associated trauma to the vascular wall. Suitable administration sites may include the internal elastic lamina, where, preferably, the disclosed compositions do not include elastases. All debris is will be aspirated, thereby avoiding any risk of embolization.

Example 2—A New Paradigm for Treating Atherosclerotic Lesions

The following Example is derived from a abstract of a presentation given at the 10$^{th}$ Annual Arteriosclerosis, Thrombosis and Vascular Biology Conference on May 1, 2009.

Summary.

Severe atherosclerotic disease is commonly treated via percutaneous interventions, such as angioplasty, stenting, cryoplasty, or mechanical atherectomy. However, these techniques either fail to reduce atherosclerotic plaque burden or reduce plaque burden without causing arterial injury. The aim of this study is to evaluate a novel method of treating atherosclerotic plaques that does not induce injury to the vascular wall: in vitro plaque dissolution and digestion.

Methods.

Atherosclerotic plaques were obtained from patients undergoing endarterectomies. The optimal concentration and conditions for plaque dissolution and digestion were determined for ethylenediaminetetraacetic acid (EDTA), β-cyclodextrin, and collagenase type I, III, IV, and V. Variables that were assessed included: 1) combination of different agents, 2) time, 3) temperature, 4) pH, and 5) agitation. Weight of each specimen was measured at different time points to determine percent of undigested plaque.

Results.

It was determined that a combination of type I, III, IV, and V collagenase at a concentration of 4 mg/ml resulted in 48.2% reduction of plaque at 2 hours (p<0.05). This combination was significantly more effective than each collagenase alone, or other combinations thereof (P<0.05). It also was determined that increasing temperature from 37° to 44° Celsius increased efficacy by 10%, and that agitation (225 rpm) increased efficacy by 9% compared to stasis. Further, optimal pH (range 7.2-7.7) was found to be 7.4 (47% reduction, p<0.05). Maximum plaque digestion occurred upon first exposing the plaque to a dissolution solution consisting of β-cyclodextrin and EDTA for 15 minutes, then changing the solution to collagenases (I, III, IV, V) at a temperature of 44° Celsius, pH 7.4, and agitation at 225 rpm (61% reduction, t=2 hrs, p<0.05). Neither EDTA or β-cyclodextrin alone caused significant reduction in plaque weight (15% and 2%, respectively, p<0.05).

Conclusion.

Effective plaque dissolution and digestion was observed in vitro. These data serve as the foundation for further refinements of this technique in order to reduce digestion time. This research has the potential to dramatically alter standard approaches for percutaneous interventions to treat cardiovascular disease.

Example 3—Further Development of Digestion and Dissolution Solutions for Arterial Plaques Methods, Results, and Discussion.

Figure 3:
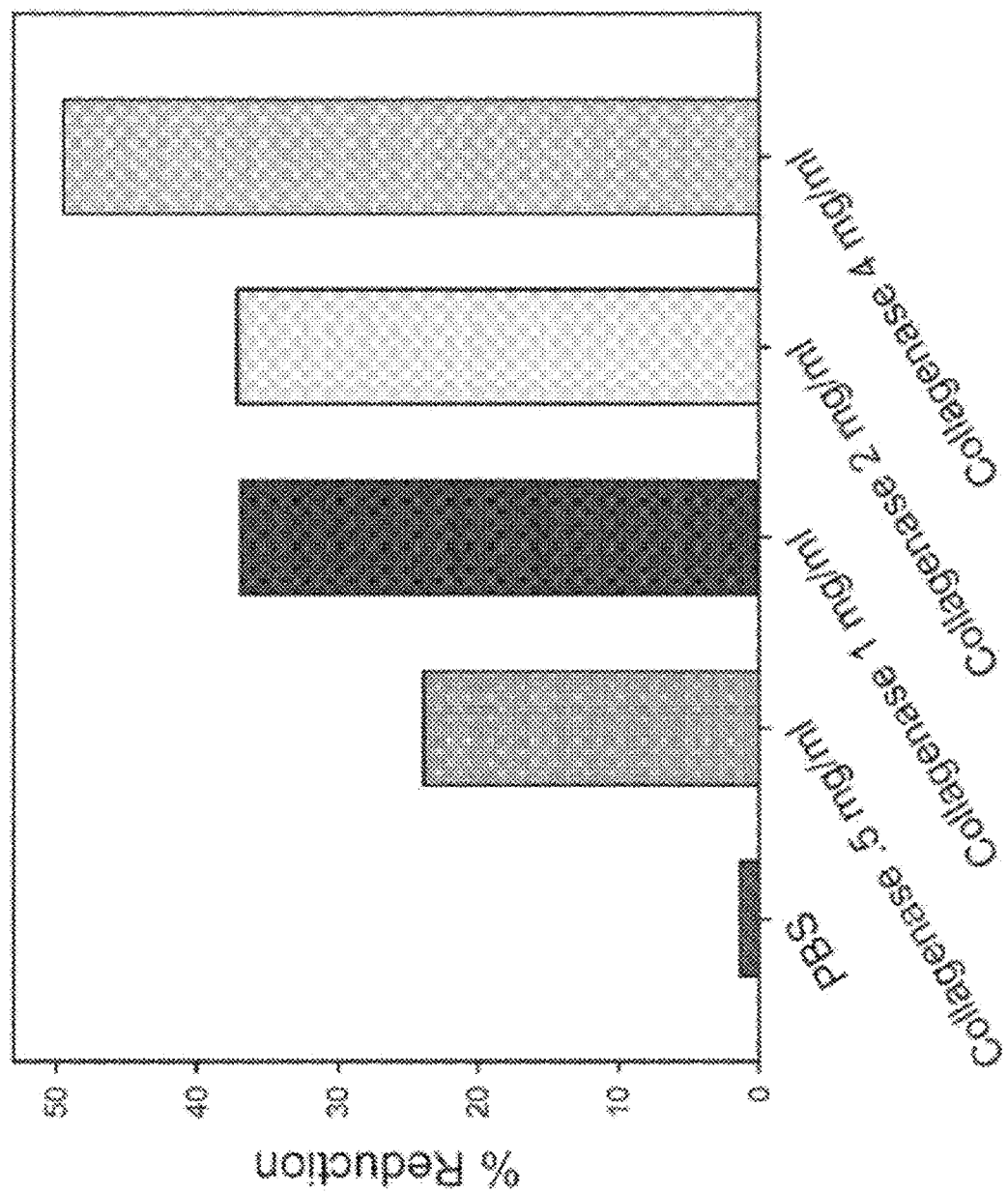
FIG. 3. illustrates digestion of plaque sections using varying concentrations of mixed collagenases solution.
Figure 4:
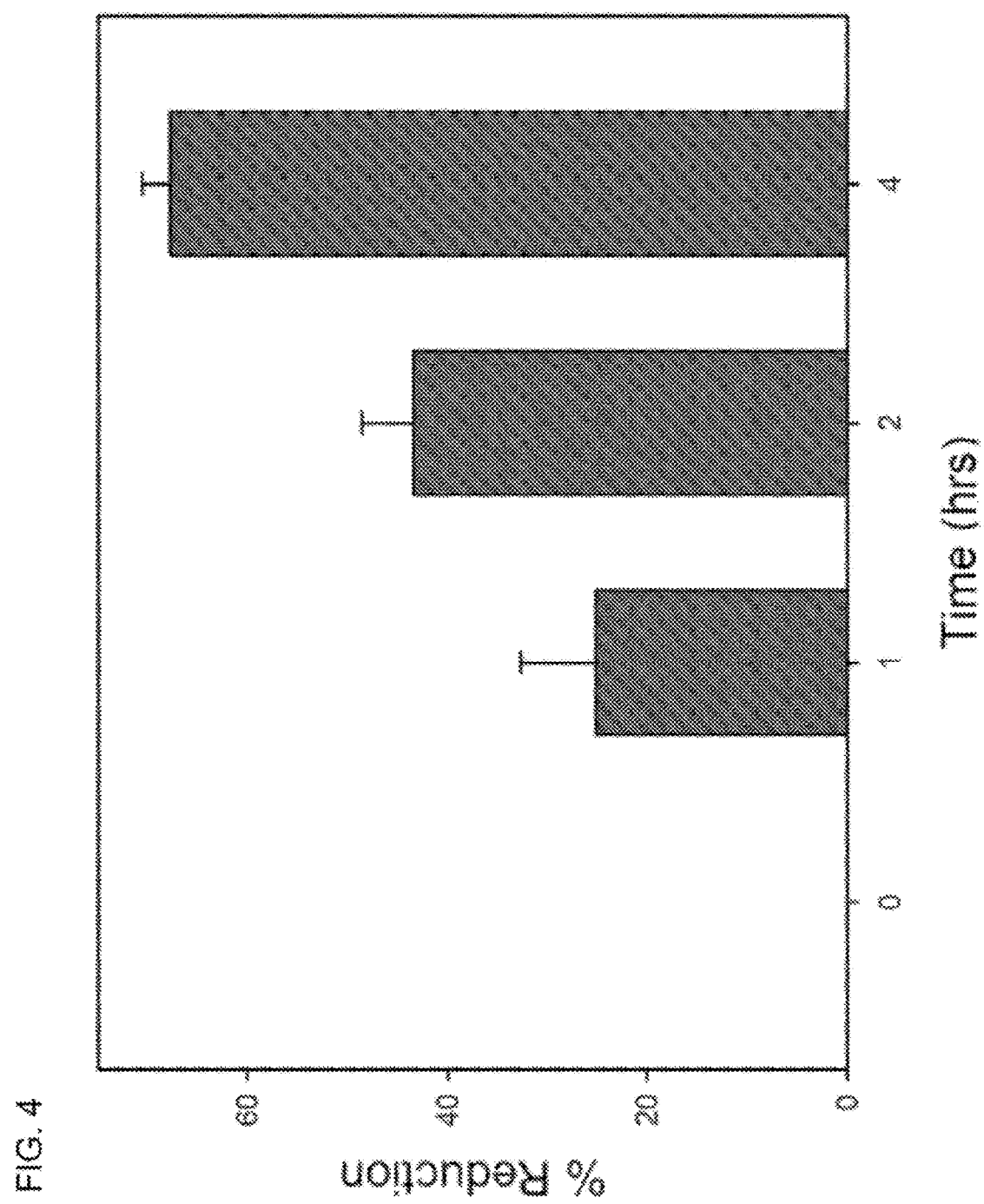
FIG. 4. illustrates digestion of full plaques over time.

A digestion solution that effectively results in 30-40% plaque digestion in vitro in 30 minutes was developed in a step-wise, methodical manner. First, collagenases were evaluated to determine feasibility of the digestion solution. Human arterial plaque samples were collected and sectioned into approximately 1>1 cm sections. To determine percent of plaque reduction, weights of the samples were measured at baseline and at designated time points. Types I, III, IV, and V collagenases were combined (1:1:1:1) at concentrations of 0.5, 1, 2, and 4 mg/ml and tested against control solution (PBS). A collagenase solution at 4 mg/ml caused the greatest percent reduction of plaque weight over control after 2 hrs in solution (50% versus 1%, respectively, p<0.05; FIG. 3). To determine if cutting the plaque into 1×1 cm sections enhanced digestion compared to full plaques, digestion of full plaques was evaluated. FIG. 4 shows that full plaques demonstrated similar reduction in plaque mass as compared to plaque sections (FIG. 4).

Figure 5:
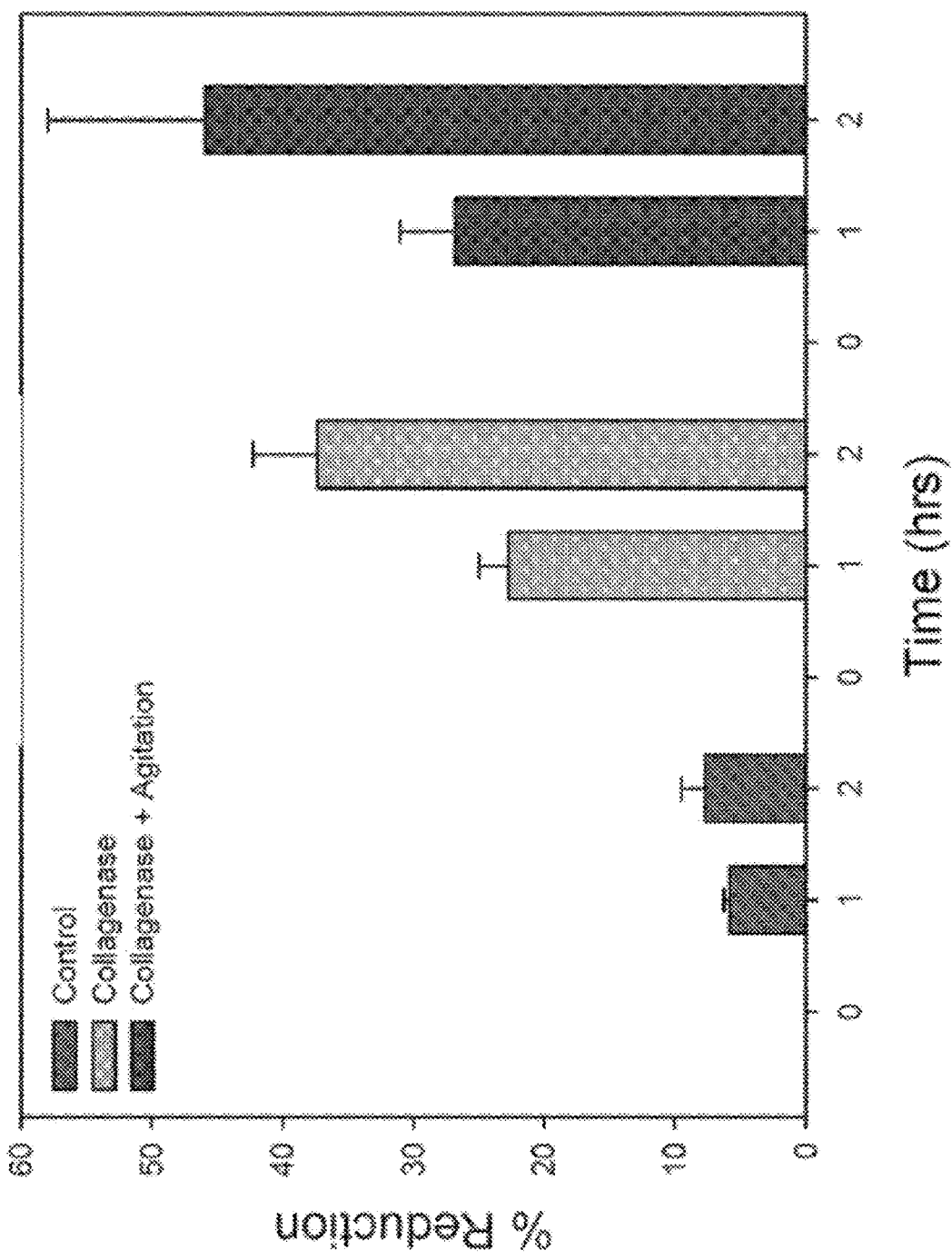
FIG. 5. illustrates digestion of plaque section using agitation.
Figure 6:
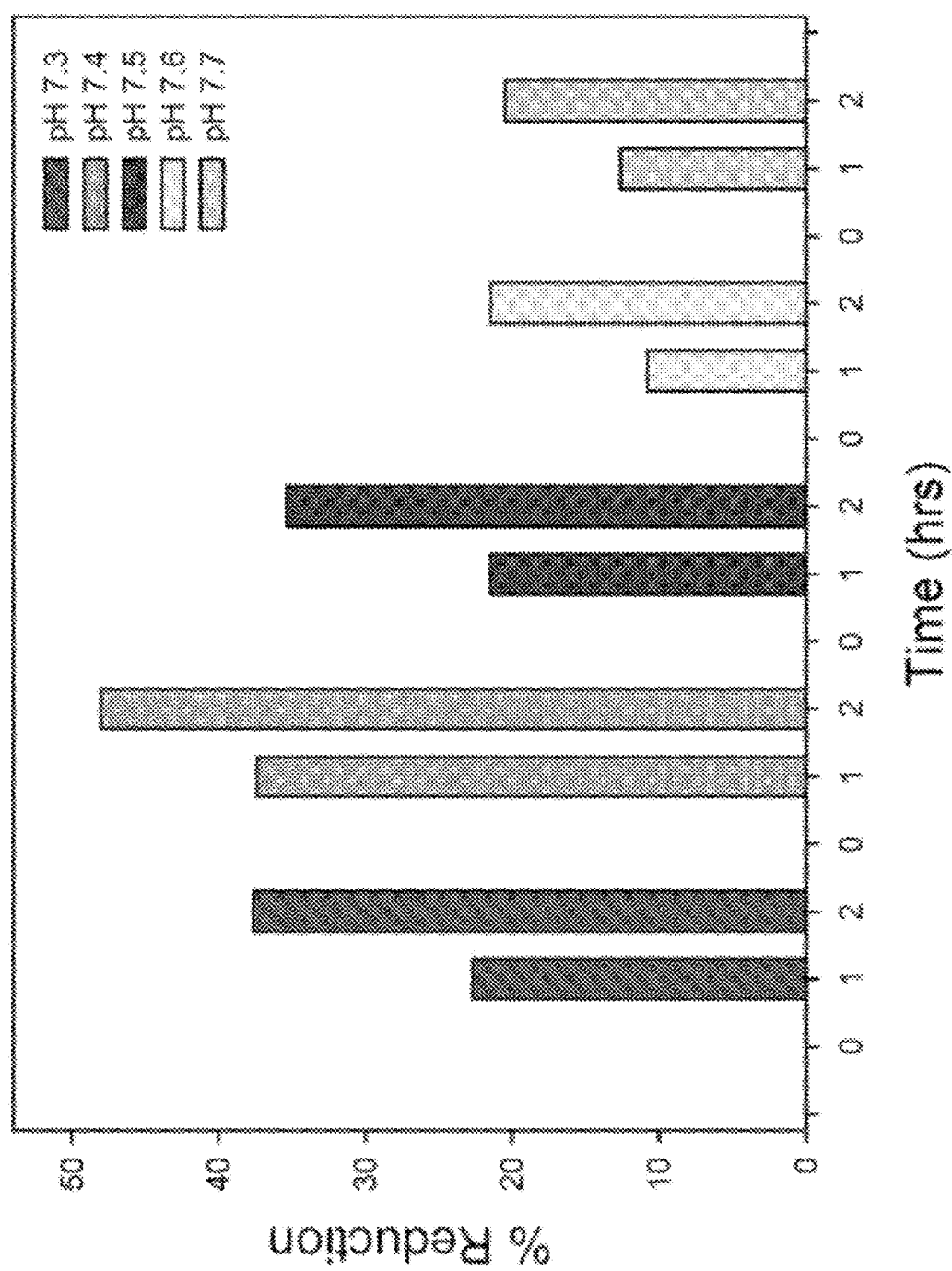
FIG. 6. illustrates the effect of pH on digestion of plaque sections.
Figure 7:
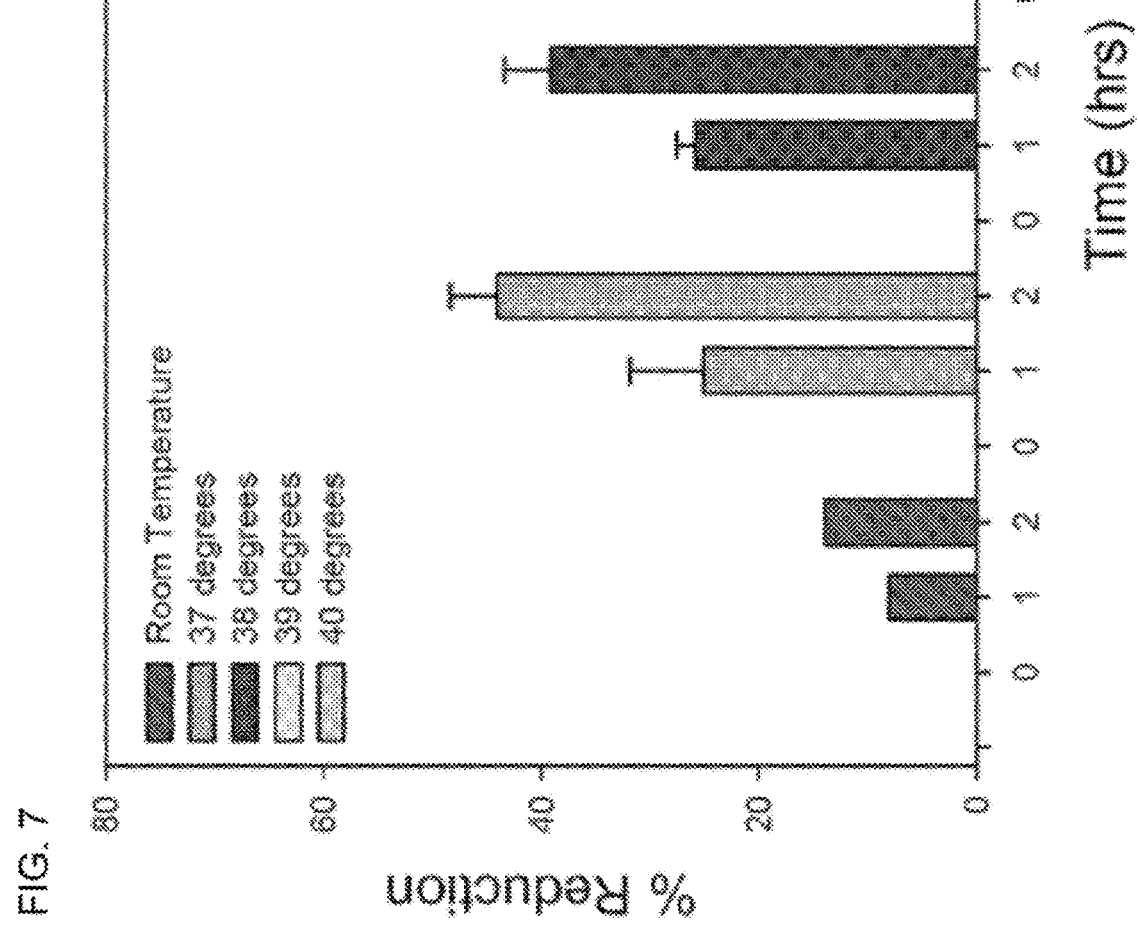
FIG. 7. illustrates the effect of temperature on digestion of plaque sections.

To establish optimal conditions for the collagenase solution, various parameters were modified and evaluated with respect to enhancing digestion. First, the effect of agitation on plaque reduction was evaluated. Using the collagenase mixture, plaque specimens were exposed to static conditions or agitation with a shaker at 225 rpm. Plaque specimens that were exposed to agitation had greater reduction versus static conditions (46% versus 37%, t=2 hrs; FIG. 5). The effect of pH on the collagenase solution was then evaluated. Plaque specimens digested with a solution at pH 7.4 showed the greatest percent reduction (48% reduction at 2 hrs; FIG. 6). Finally, optimal temperature for the digestion solution was established. Digestion was evaluated at room temperature, and between 37-40° C. The collagenase solution was more effective with increasing temperature (58% at 2 hrs; FIG. 7).

Figure 8:
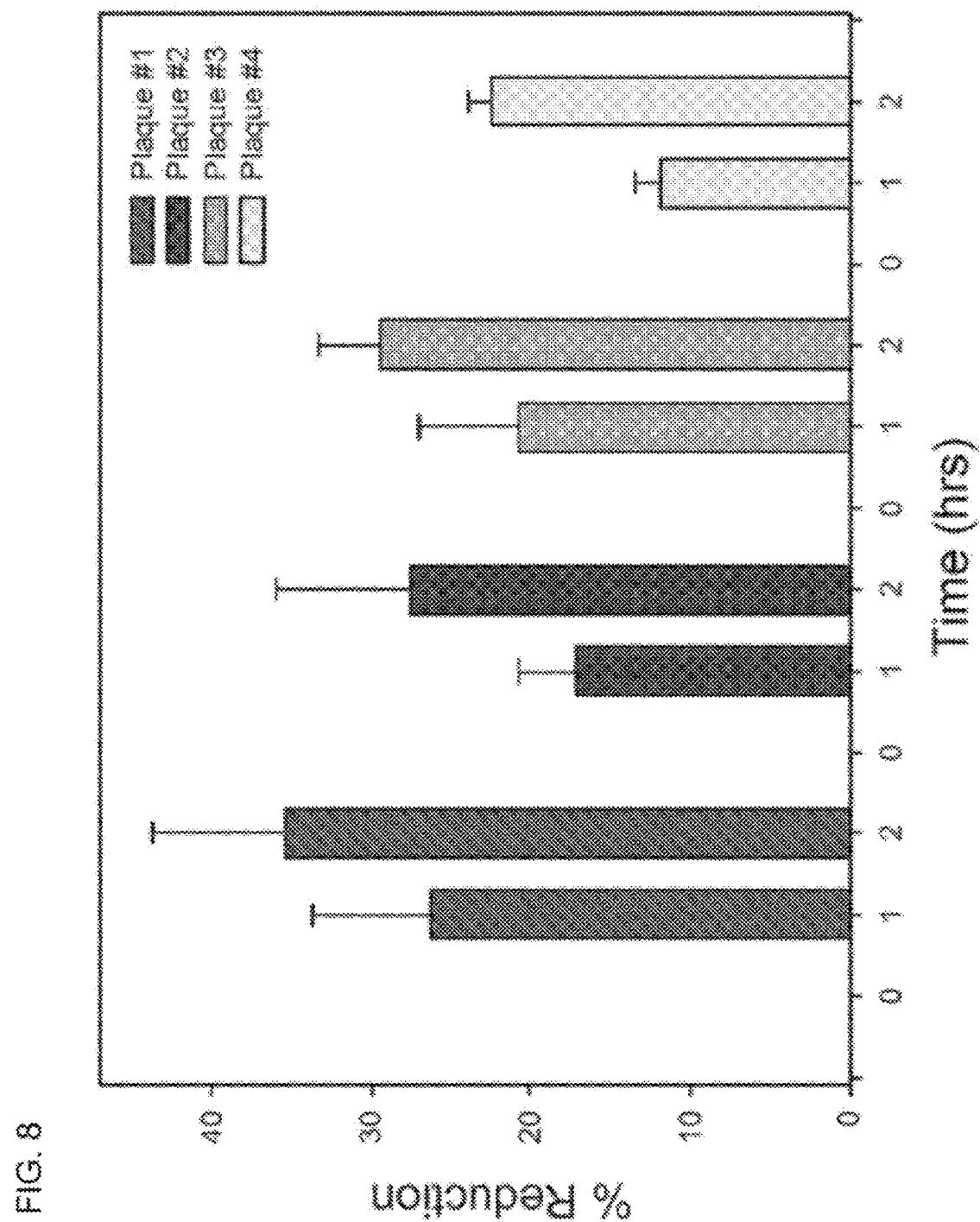
FIG. 8. illustrates digestion of plaque sections from different patients.
Figure 9:
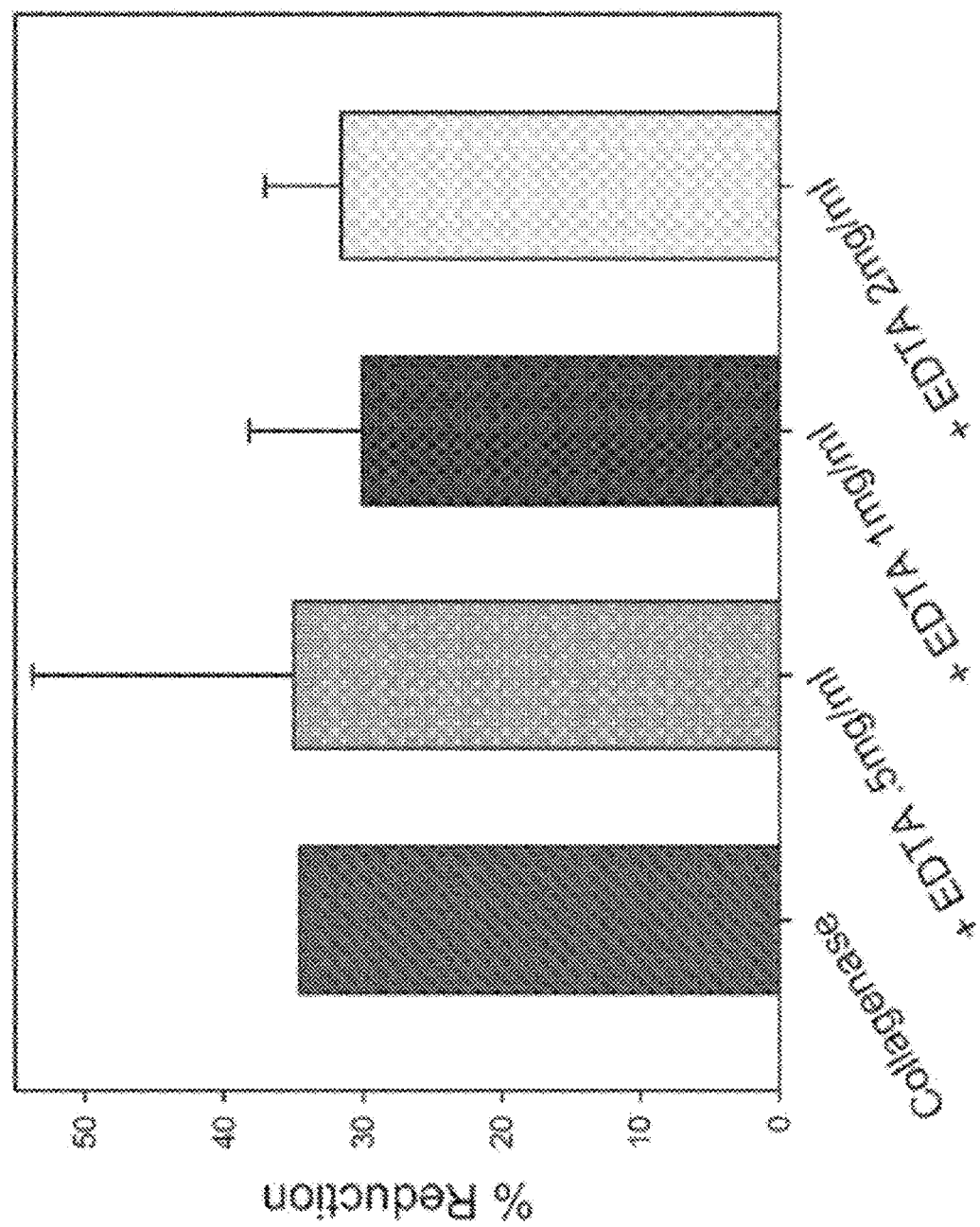
FIG. 9. illustrates the effect of EDTA on digestion of plaque sections.
Figure 10:
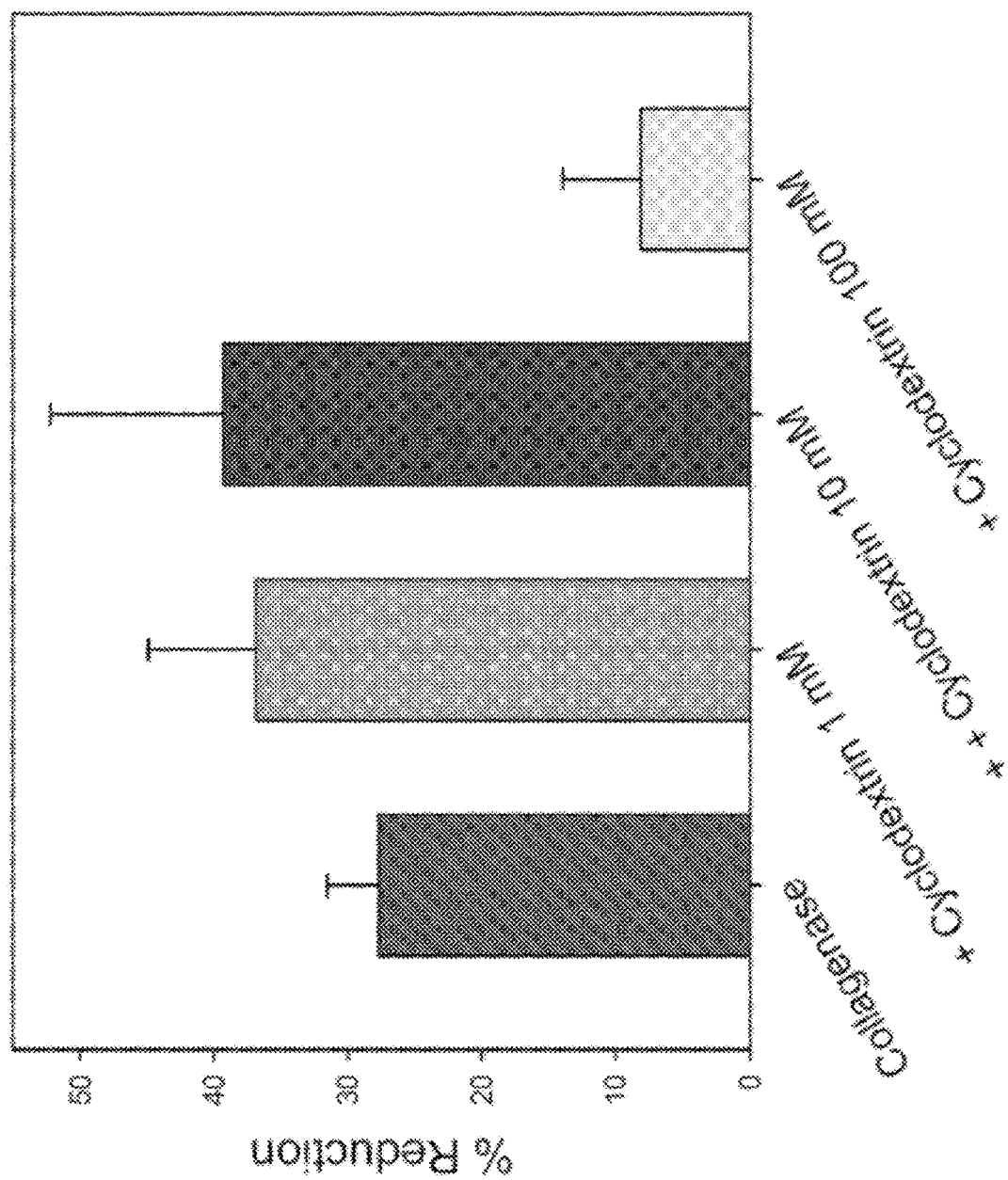
FIG. 10. illustrates the effect of cyclodextrin on digestion of plaque sections.
Figure 11:
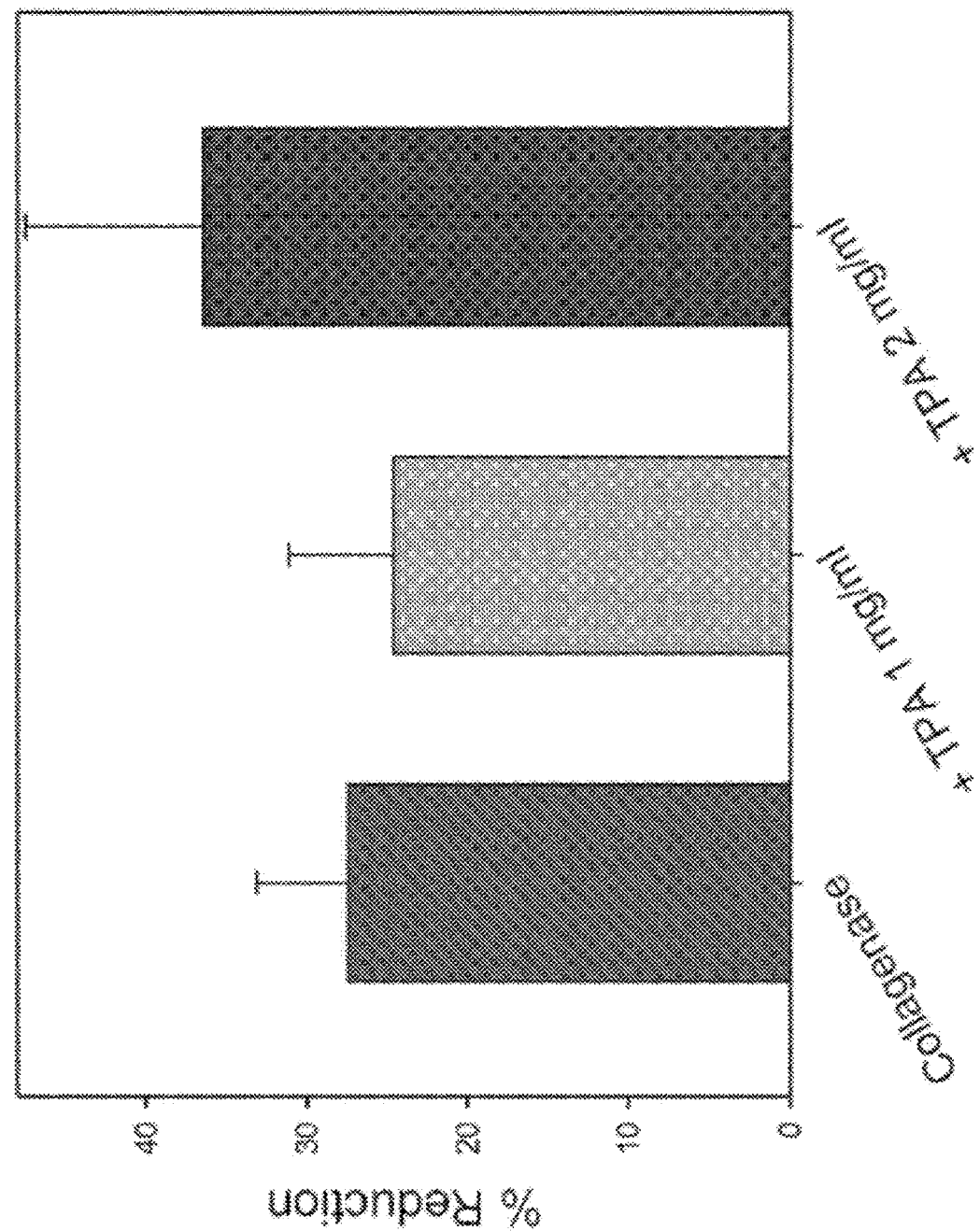
FIG. 11. illustrates the effect of tPA on digestion of plaque sections.

After implementing optimal digestion conditions with respect to agitation, pH, and temperature, the effect of the digestion solution was evaluated on plaques harvested from different patients. Differences were observed wither respect to reduction in plaque mass when exposing different plaque specimens to the digestion solution (FIG. 8), presumably due to intra-species plaque variability due to different amounts of calcification, lipids, and plaque hemorrhage within the plaques from different patients. Thus various agents were tested in combination with collagenase to determine if an enhanced reduction of plaque mass could be achieved regardless of intra-species variability. To evaluate the effect of localized chelation from the plaque, ethylenediaminetetraacetic acid (EDTA) was added to the collagenase solution. Given that EDTA is a calcium chelator and that collagenase requires calcium for activity, calcium chloride (5 mM) was added to the solution. However, a collagenase solution having EDTA showed no enhanced reduction in plaque mass compared to a collagenase solution without EDTA (FIG. 9). To remove lipid components of the plaque, β-cyclodextrin (1-100 mM) was added to the collagenase solution. Plaque specimens digested with collagenase and 10 mM β-cyclodextrin showed greatest reduction in plaque weight versus collagenase alone (39% versus 28% at 1 hr; FIG. 10). The effect of tissue plasminogen activator (tPA) also was assessed with respect to dissolving proteoglycans and thrombus within the plaque. Samples were exposed to collagenase, or collagenase with tPA (1-2 mg/ml). Tissue plasminogen activator at 2 mg/ml with collagenase demonstrated the greatest percent reduction versus collagenase alone (37% vs. 27% at 1 hr; FIG. 11).

Figure 12:
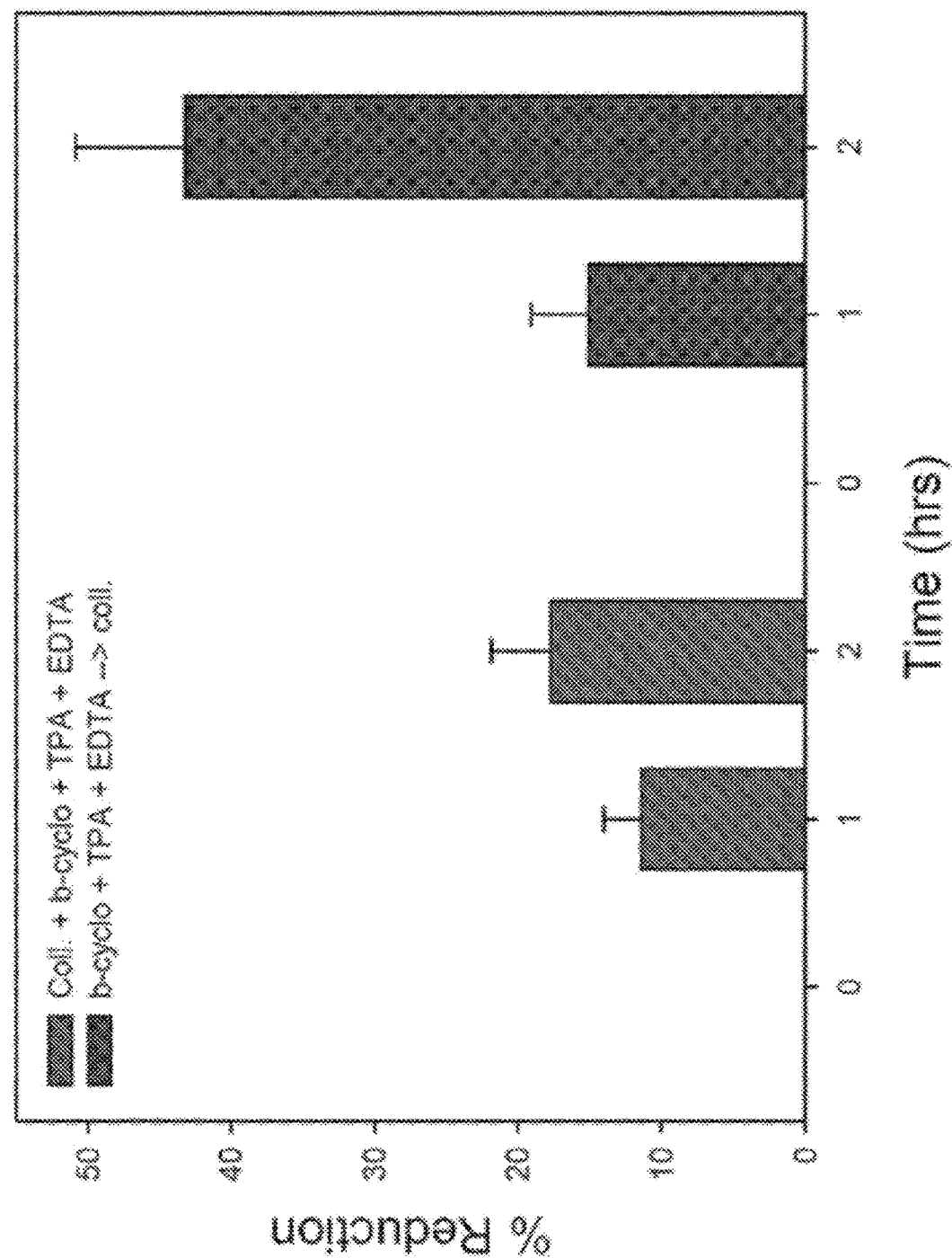
FIG. 12. illustrates the effect of adding a "dissolution" solution (β-cyclodextrin, tPA, and EDTA) prior to adding a "digestion" solution comprising a collagenase mixture (I, III, IV, and V).
Figure 13:
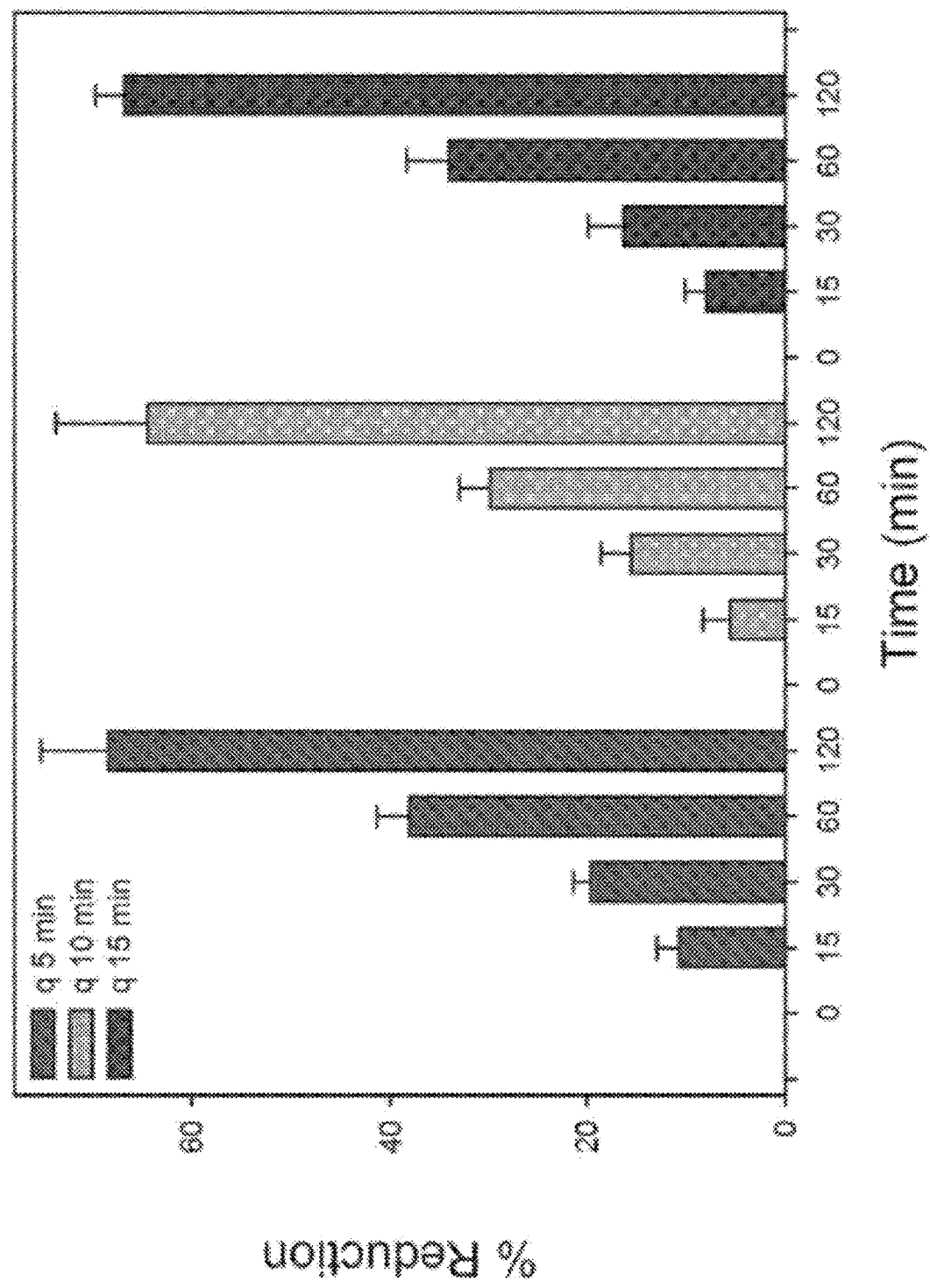
FIG. 13. illustrates the effect of adding a "dissolution" solution 5, 10, or 15 minutes prior to adding a "digestion" solution.
Figure 14:
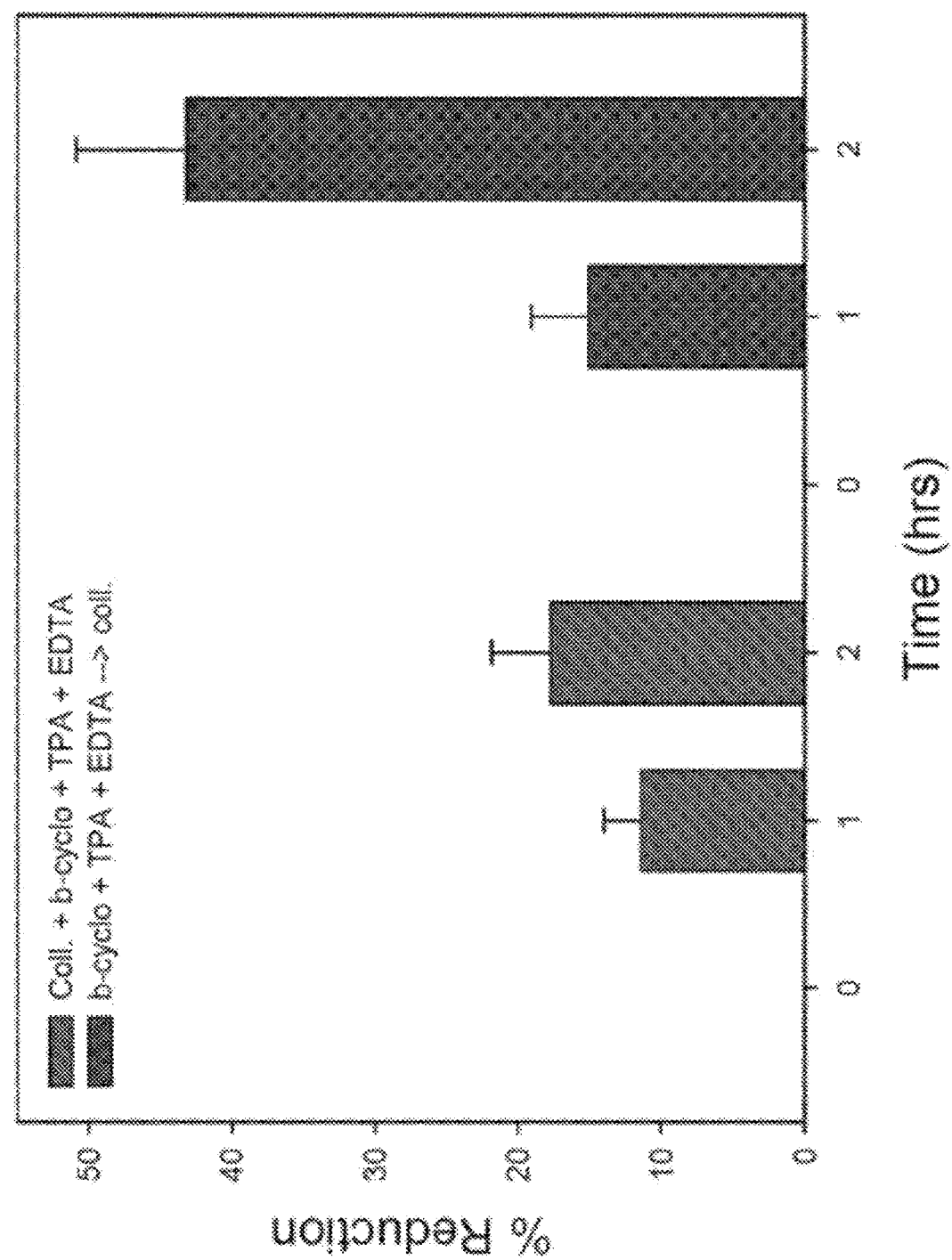
FIG. 14. illustrates greater than 40% digestion of a human atherosclerotic plaque within 60 min (and >60% digestion by 120 min) by optimizing collagenase, EDTA, calcium, β-cyclodextrin, tPA, temperature, pH, agitation, and time.
Figure 15:
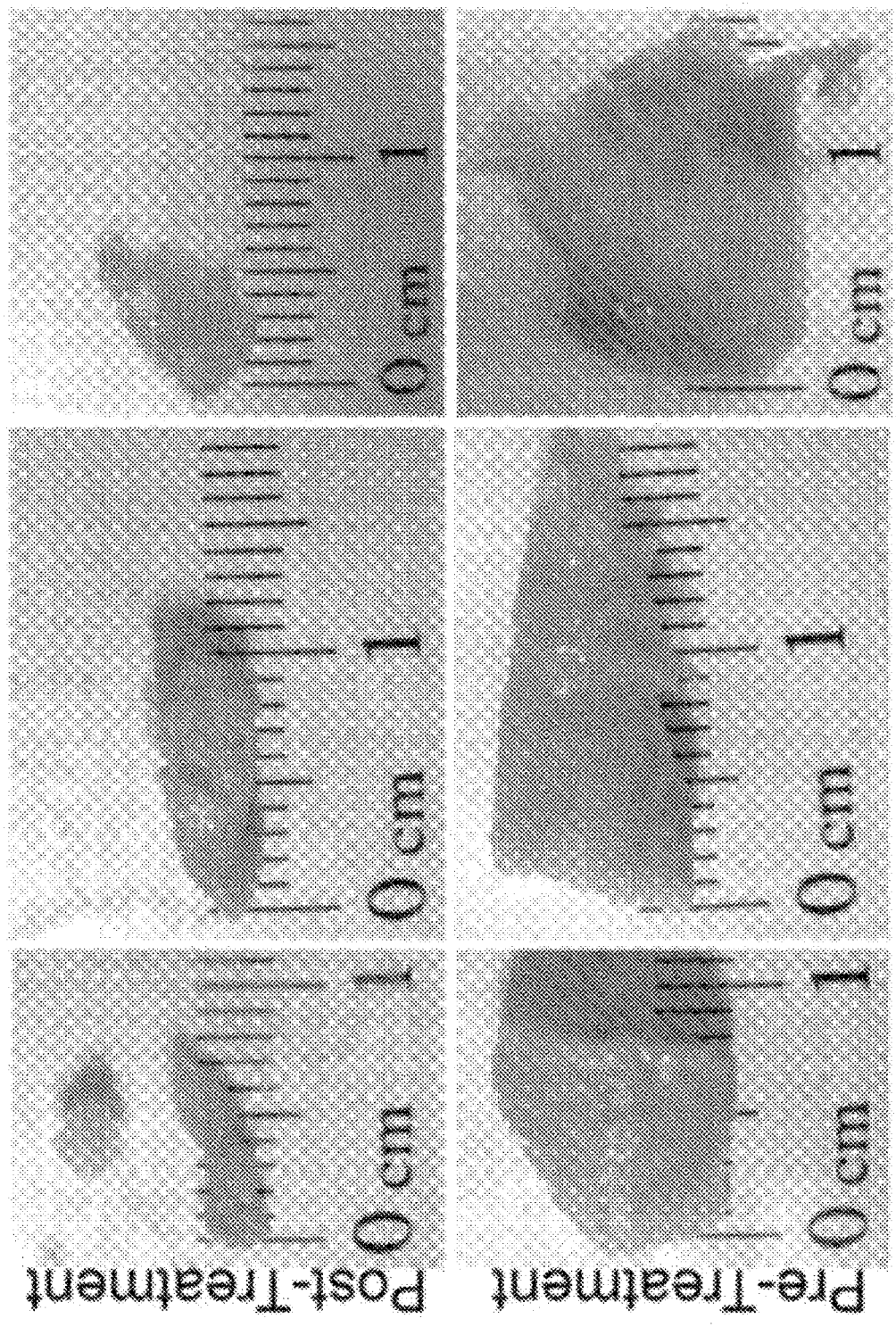
FIG. 15. provides photographs of plaques before and after treatment with the dissolution and digestion compositions after 30 minutes.

Given the potential of the various agents (i.e., EDTA, β-cyclodextrin, tPA, etc.) for enhancing plaque mass reduction, the agents were evaluated further in various different combinations and different temporal arrangements with the collagenases. First, we tested whether collagenase was more effective with all agents combined or if a "dissolution" solution consisting or these agents would enhance the effect of collagenase if exposed to the plaque first. Indeed, the "dissolution" solution of EDTA, calcium, β-cyclodextrin, and tPA when added 1 hr prior to the "digestion" solution consisting of solely the combination of the various collagenases was significantly more effective versus a combination of the "dissolution" and "digestion" solution together (44% vs. 18% at 2 hrs; FIG. 12). To investigate how long to keep the plaque in the "dissolution" solution prior to adding it to the "digestion" solution, it was observed that maintaining the plaque in the "dissolution" solution for 15 minutes then adding the "digestion" solution was optimal (FIG. 13). By optimizing collagenase, EDTA, calcium, β-cyclodextrin, tPA, temperature, pH, agitation, and time, we have been able to achieve 40% digestion of a human atherosclerotic plaque within 60 min, and >60% digestion by 120 min (FIGS. 14 and 15).

Future Directions.

Successful plaque digestion was performed in vitro with dissolution and digestion solutions. Next, the dissolution and digestion solutions will be evaluated on intact human atherosclerotic arteries using an ex vivo perfusion circuit with a goal of achieving significant plaque digestion in a clinically relevant time. Given that the presently disclosed methods may be performed repeatedly, a 50% plaque digestion within 10 minutes is clinically significant. To safeguard against the possibility of digesting too much of the arterial wall, preferably the dissolution and/or digestion solutions utilized in the methods do not include elastases. Thus, digestion preferably is limited to the atherosclerotic plaque, above the internal elastic lamina.

An ex vivo perfusion circuit will be assembled from the following components: an LED micrometer, specialty chamber, computer, software, interface boards, Masterflow™ pump software, DB9 cable assemblies, L/S Easy Load™ pump head, L/S brushless programmable drive, Masterflex Pharmed™ tubing LS/17, Masterflex™ silicone tubing LS/17, and Top Works™ bottle top tubing. After successfully establishing the ex vivo perfusion circuit, the efficacy of the dissolution and digestion solutions will be evaluated using intact human atherosclerotic arteries. Atherosclerotic arteries will be harvested from limb amputation specimens. After the artery is harvested, it will be weighed then secured to the perfusion circuit. The artery will be preserved in a normal saline perfusate. Ultrasonography of the artery will be performed to quantify the atherosclerotic bulk. After documentation of the plaque, flow inside the lumen of the artery will be occluded with externally applied non-traumatic vascular clamps. The digestion solution will be injected into the lumen of the artery via an angiocatheter through one end of the artery prior to occlusion. After 10-min increments, the digestion solution will be evacuated and transferred to a 15 ml conical vial for later evaluation. The artery will be weighed, returned to the perfusion circuit, and undergo ultrasound assessment of the atherosclerotic plaque. Fresh digestion solution will be instilled and the process will be repeated three times (i.e., 10-min, 20-min, and 30-min time points). The weight of the artery will be correlated with the atherosclerotic plaque bulk as measured by ultrasonography. After successfully establishing a baseline, the digestion solution will be optimized to achieve the greatest plaque reduction in the least amount of time. To do this, the number of applications of fresh solution, time, temperature, pH, and agitation will be varied, similar to the in vitro studies. In addition, further refinements in the constituents and concentrations of the constituents of the dissolution and digestion solution will be performed, as well as the inclusion of additional agents.

The studies described above are expected to: 1) demonstrate efficacy of a digestion solution in an ex vivo perfusion circuit with a human atherosclerotic artery, and 2) optimize the efficacy of digestion solution to achieve 50% plaque digestion within 10 min in this ex vivo perfusion circuit. Additional agents that solubilize hydrophobic molecules may be included in the dissolution or digestion solutions, such as cholesterol, or hydrolyzed cholesterol esters. Additionally, different proteases other than collagenases may be included.

In the foregoing description, certain terms have been used for brevity, clearness, and understanding. No unnecessary limitations are to be implied therefrom beyond the requirement of the prior art because such terms are used for descriptive purposes and are intended to be broadly construed. The different compositions and method steps described herein may be used alone or in combination with other compositions and method steps. It is to be expected that various equivalents, alternatives and modifications are possible. The cited patent and non-patent references are incorporated by reference in their entireties. The definitions provided in the present specification supersede any definition for a term provided in a cited reference.

The invention claimed is:

1. A method for digesting a human arterial plaque within an artery of a patient the method comprising:
   (a) contacting the arterial plaque with a pharmaceutical composition comprising a collagenase mixture consisting of collagenase type I collagenase type III, collagenase type IV, and collagenase type V by administering the composition to the patient via a double-balloon catheter, wherein each of the collagenase type I, collagenase type III, collagenase type IV, and collagenase type V is present in the composition at a concentration of at least 0.5 mg/ml: and (b) applying ultrasonic energy at a frequency of 10-100 kHz to the arterial plaque during contacting the arterial plaque with the composition, wherein the ultrasonic energy is applied for u period of time sufficient to reduce mass of the arterial plaque by at least 30%.

2. The method of claim 1, wherein the composition further comprises a cyclodextrin at a concentration of 5-25 mM.

3. The method of claim 1, wherein the composition further comprises a chelating agent at a concentration of 0.75-1.25 mg/ml.

4. The method of claim 1, wherein the composition further comprises tissue plasminogen activator at a concentration of 0.75-1.25 mg/ml.

5. The method of claim 1, wherein the composition further comprises cholesterol esterase at a concentration of 0.1-10 units/ml.

6. The method of claim 1, wherein the composition further comprises lipoprotein lipase at a concentration of 30-10,000 units/ml.

7. The method of claim 1, wherein the composition further comprises apolipoprotein CII at a concentration of 1-20 units/ml.

8. The method of claim 1, wherein the composition further comprises phospholipase A2.

9. The method of claim 1, wherein the composition further comprises pepsin at a concentration of 1-50 mg/ml.

10. The method of claim 1, wherein the composition has a pH of about 7.2-7.6.

11. The method of claim 1, wherein the composition further comprises calcium chloride.

* * * * *